United States Patent
Cox et al.

(10) Patent No.: US 10,155,771 B2
(45) Date of Patent: Dec. 18, 2018

(54) SELECTIVE REDUCTION OF MORPHINAN ALKALOIDS

(71) Applicant: Noramco Inc., Wilmington, DE (US)

(72) Inventors: D. Phillip Cox, Eagleville, PA (US); C. Oliver Kappe, Graz (AT); Bartholomaus Pieber, Graz (AT)

(73) Assignee: Noramco, Inc., Wilmington, DE (US)

( * ) Notice: Subject to any disclaimer, the term of this patent is extended or adjusted under 35 U.S.C. 154(b) by 0 days.

(21) Appl. No.: 15/343,714

(22) Filed: Nov. 4, 2016

(65) Prior Publication Data
US 2017/0137432 A1 May 18, 2017

Related U.S. Application Data

(60) Provisional application No. 62/250,856, filed on Nov. 4, 2015.

(51) Int. Cl.
*C07D 489/02* (2006.01)

(52) U.S. Cl.
CPC .................. *C07D 489/02* (2013.01)

(58) Field of Classification Search
None
See application file for complete search history.

(56) References Cited

U.S. PATENT DOCUMENTS

| 3,812,132 A | 5/1974 | Grew et al. |
| 4,668,685 A * | 5/1987 | Shami .................. C07D 221/28 514/279 |
| 8,399,671 B2 | 3/2013 | Orr et al. |
| 8,921,557 B2 | 12/2014 | Weber et al. |
| 2006/0009479 A1 | 1/2006 | Bailey et al. |
| 2015/0252052 A1 | 9/2015 | Matharu et al. |

OTHER PUBLICATIONS

Carroll et al, Journal of Organic Chemistry, vol. 74 No. 2, pp. 747-752 (Year: 2009).*
Eppenberger et al., "Stereochemie der Umwandlung von Dihydrothebain in Thebain Synthese von Markierten Thebaine", Helvetica Chimica Acta (1968), vol. 51, pp. 381-397.
Hessel et al., "Novel Process Windows for Enabling, Accelerating, and Uplifting Flow Chemistry", ChemSusChem (2013) 6, pp. 746-789.
Pieber et al., "Continuous Flow Reduction of Artemisinic Acid Utilizing Multi-Injection Strategies—Closing the Gap Towards Fully Continuous Synthesis of Antimalarial Drugs", Chem. Eur. J. (2015) 21, pp. 4368-4376.
Pieber et al., "In Situ Generation of Diimide from Hydrazine and Oxygen: Continuous-Flow Transfer Hydrogenation of Olefins", Angew. Chem. Int. Ed. (2013) 52, pp. 10241-10244.

* cited by examiner

*Primary Examiner* — Zinna Northington Davis
(74) *Attorney, Agent, or Firm* — Alston & Bird LLP

(57) ABSTRACT

The present disclosure relates to selective reduction of morphinan alkaloids in a continuous flow system. In particular, the present disclosure relates to selective reduction of thebaine or oripavine using hydrazine or a hydrazine-containing compound in a continuous flow system under elevated temperature and pressure condition to form 8,14-dihydrothebaine or 8,14-dihydrooripavine, respectively.

27 Claims, 16 Drawing Sheets

Production of hydrocodone (1) from codeine (2); from codeine (2) via dihydrocodeine (3); or from thebaine (4) via 8,14-dihydrothebaine (5)

Exemplary continuous flow reactor system for the *in situ* generation of diimide and subsequent olefin reductions.

FIGURE 4

| entry | T [°C] | coil (mL) | $t_{Res}$ [min] | 4 [%] | 5 [%] | 6 [%] | 7 [%] |
|---|---|---|---|---|---|---|---|
| 4-1 | 50 | PFA (13) | 10 | 81 | 9 | <1 | <1 |
| 4-2 | 100 | PFA (13) | 12 | 18 | 26 | 32 | 26 |
| 4-3 | 120 | PFA (13) | 14 | <1 | 2 | 38 | 58 |
| 4-4 | 140 | PFA (13) | 16 | <1 | <1 | 23 | 73 |
| 4-5 | 120 | SS (20) | 10 | 44 | 49 | <1 | <1 |
| 4-6 | 140 | SS (20) | 10 | 40 | 54 | <1 | <1 |

Effect of the Temperature, Time and Coil Material on Thebaine Reduction.

Effect of additives, pressure and oxygen gas flow rate in the continuous reduction of thebaine.

| entry | N₂H₄·H₂O [equiv] | T [°C] | $t_{Res}$ [min] | 4 [%] | 5 [%] |
|---|---|---|---|---|---|
| 6-1 | 4 | 100 | 10 | 37 | 61 |
| 6-2 | 4 | 120 | 8 | 26 | 72 |
| 6-3 | 3 | 120 | 8 | 27 | 71 |
| 6-4 | 2 | 120 | 8 | 42 | 56 |
| 6-5 | 4 | 140 | 6 | 25 | 74 |
| 6-6 | 3 | 140 | 6 | 23 | 74 |
| 6-7 | 2 | 140 | 6 | 41 | 58 |

Effect of temperature and hydrazine stoichiometry in the continuous reduction of thebaine.

HPLC-UV chromatogram (215 nm) of the thebaine reduction with diimide at 10 bar and 120°C in the presence of dimethylsulfide (Figure 6-3).

Exemplary multi-injection continuous flow system for the *in situ* generation of diimide. The basic setup (RTU-1) is extended by two additional feeds (i.e., P2 and P3) with the respective residence time units (i.e., RTU-2 and RTU-3).

FIGURE 9

| entry | N$_2$H$_4$·H$_2$O [equiv] | RTU [mL] | t [min] | 4 [%] | 5 [%] |
|---|---|---|---|---|---|
| 9-1 (O$_2$ flow 10 mL/min) | 3+3 | 2×10 | 17 | 14 | 83 |
| 9-2 (O$_2$ flow 10 mL/min) | 3+0 | 2×10 | 17 | 29 | 69 |
| 9-3 (O$_2$ flow 5 mL/min) | 3+3 | 2×10 | 30 | 28 | 70 |
| 9-4 (O$_2$ flow 10 mL/min) | 3+3+3 | 3×10 | 26 | 7 | 90 |
| 9-5 (O$_2$ flow 10 mL/min) | 3+3+3+3 | 4×10 | 37 | 4 | 94 |
| 9-6 (O$_2$ flow 10 mL/min) | 3+1+1+1 | 4×10 | 35 | 9 | 87 |
| 9-7 (O$_2$ flow 10 mL/min) | 3+3+3+3+3 | 5×10 | 50 | 5 | 94 |

Reduction of thebaine using multi-injection of hydrazine hydrate.

Continuous transfer hydrogenation and batch hydrolysis for the synthesis of hydrocodone from thebaine.

Additive Screening.

Table

| entry | solvent | [M] | TSH [equiv] | ETA [equiv] | T [°C] | t [min] | conversion [%] |
|---|---|---|---|---|---|---|---|
| 13-1 | EtOH | 0.4 | 2 | 2 | 100 | 20 | 75 |
| 13-2 | EtOH | 0.4 | 2 | 2 | 120 | 20 | 94 |
| 13-3 | EtOH | 0.4 | 2 | 2 | 130 | 20 | 92 |
| 13-4 | Toluene:EtOH (1:1) | 0.2 | 2 | 2 | 120 | 20 | 93 |
| 13-5 | Toluene:EtOH (1:1) | 0.2 | 2 | 2 | 120 | 10 | 73 |
| 13-6 | Toluene:EtOH (1:1) | 0.2 | 2 | 2 | 120 | 30 | 96 |
| 13-7 | Toluene:EtOH (1:1) | 0.2 | 2 | 2 | 120 | 120 | 97 |
| 13-8 | Toluene:EtOH (1:1) | 0.2 | 2 | 3 | 120 | 20 | 95 |
| 13-9 | Toluene:EtOH (1:1) | 0.2 | 2.5 | 2 | 120 | 20 | 97 |
| 13-10 | Toluene:EtOH (1:1) | 0.2 | 3 | 3 | 120 | 20 | 98 |

Batch experiments for the reduction of thebaine using *p*-toluenesulfonyl hydrazide.

Continuous transfer hydrogenation of thebaine using TSH.

| entry | c [M] | ETA [equiv] | TSH [equiv] | RTU 1/2 [mL] | Flow 1/2 [μL min$^{-1}$] | $t_{Res}$ [min] | 4 [%]$^b$ | 5 [%]$^b$ |
|---|---|---|---|---|---|---|---|---|
| 15-1 | 0.2 | 2 | 2 | 10/-- | 250/-- | 40 | 6 | 93 |
| 15-2 | 0.15 | 3 | 3 | 10/-- | 250/-- | 40 | 5 | 93 |
| 15-3 | 0.12 | 4 | 4 | 10/-- | 250/-- | 40 | 3 | 96 |
| 15-4 | 0.3 | 2 | 1+1 | 10/10 | 300/480 | 92 | 6 | 92 |
| 15-5 | 0.3 | 2 | 1+1 | 10/20 | 250/400 | 90 | 3 | 95 |
| 15-6 | 0.3 | 3 | 1.5+1.5 | 10/20 | 250/400 | 90 | <1 | 97 |
| 15-7 | 0.3 | 3 | 1.5+1.5 | 10/20 | 500/800 | 45 | <1 | 97 |

Optimization of the Thebaine Reduction Using TSH in Flow.

SELECTIVE REDUCTION OF MORPHINAN ALKALOIDS

CROSS REFERENCE TO RELATED APPLICATIONS

This application claims priority to Provisional Application No. 62/250,856, filed Nov. 4, 2015, which is incorporated herein by reference in its entirety.

FIELD OF TECHNOLOGY

The present disclosure relates to selective reduction of morphinan alkaloids in a continuous flow system. In particular, the present disclosure relates to selective reduction of thebaine using hydrazine or a hydrazine-containing compound in a continuous flow system under elevated temperature and pressure condition.

BACKGROUND

Hydrocodone is a non-natural opioid and one of the most prescribed narcotic drugs. It is primarily used as an orally administered analgesic and antitussive either formulated with acetaminophen or as pure substance. Hydrocodone manufacture and consumption has steadily increased over the past 20 years.

Hydrocodone can be produced by a number of different semi-synthetic pathways, such as from codeine or thebaine. FIG. 1 shows examples of some of these synthetic routes. Codeine is often used as a precursor for hydrocodone synthesis. Codeine is found in the opium poppy plant (*papaver somniferum*), Codeine can also be obtained by a semi-synthetic pathway from morphine. Codeine can be converted directly to hydrocodone by a single isomerization of the allylic alcohol using ruthenium or rhodium based catalysts. Alternatively, codeine can be converted to dihydrocodeine by transition metal-catalyzed hydrogenation which can then he transformed into hydrocodone by an Oppenauer-type oxidation.

Thebaine can also be as a precursor for hydrocodone synthesis, and, like codeine is also present in the poppy plant, albeit in a lower amount. The generally low amount of thebaine in the opium latex or poppy straw can be significantly enriched by a mutagenized poppy plant, resulting in a remarkable increase of the thebaine production. Thebaine is an attractive precursor to use because it has limited therapeutic use. A direct transformation of thebaine into hydrocodone, however, is not feasible, but a common two-step synthesis can be used. See FIG. 1. Thebaine can be converted to 8,14-dihydrothebaine by a selective double bond reduction. Once formed, the 8,14-dihydrothebaine can be readily hydrolyzed under acidic conditions to hydrocodone.

Unfortunately, the double bond reduction of thebaine to 8,14-dihydrothebaine is difficult. Standard hydrogenation procedures cannot be applied due to severe selectivity problems. For example, hydrogenation procedures using noble metal catalysis suffer from the over-reduction of the diene moiety and hydrogenolysis of the dihydrofuran scaffold. Selective hydrogenation using a strong hydrogenation agent, i.e., diimide ($N_2H_2$), also cannot be used because the use of diimide is expensive, uneconomical and prohibitive due to safety issues.

Diimide can predominantly reduce unpolarized carbon-carbon double bonds and can avoid the side-reactions of standard hydrogenation procedures. Yet, diimide is a highly unstable compound which is usually generated in situ. The oxidation of hydrazine (FIG. 2, Method A) and the decomposition of aryl sulfonyl hydrazides (FIG. 2, Method B) are two known methods to generate diimide in situ for subsequent olefin reductions. Sulfonyl hydrazides, such as p-toluenesulfonyl hydrazide (TSH), can be used in combination with stoichiometric amounts of a weak base to generate diimide in situ. Using organic sulfonyl hydrazides is complex and expensive. The reaction is also slow requiring the use of metal and organocatalysts to enhance the reaction rate of the initial oxidation step. A more economical (atom) and less expensive (monetary) synthetic route is oxidizing hydrazine with oxygen gas ($O_2$) to form diimide in situ. This synthetic route has been discouraged in the literature, however, as involving serious safety concerns ("This process involved the use of gaseous oxygen, which is hazardous on an industrial scale since mixtures of hydrazine vapour and oxygen are potentially explosive, and employed a molar ratio of hydrazine to thebaine of 53:1 which is commercially unattractive" U.S. Pat. No. 3,812,132 (1974), the disclosure of which is incorporated herein in its entirety).

These concerns have been addressed by the present disclosure which relates to selective reduction of morphinan alkaloids, including thebaine to 8,14-dihydrothebaine, using diimide generated in situ in a continuous flow system.

SUMMARY

The present disclosure relates to selective reduction of morphinan alkaloids in a continuous flow system. In particular, the present disclosure relates to selective reduction of thebaine using hydrazine or a hydrazine-containing compound in a continuous flow system under elevated temperature and pressure conditions.

In one embodiment, the present disclosure relates to a process for the selective reduction of one or more olefin compounds, particularly one or more morphinan alkaloids, including the steps of providing a liquid mixture of the one or more olefin compounds, particularly one or more morphinan alkaloids, and hydrazine in a solvent, and contacting the liquid mixture with a gaseous oxidant to form a reaction mixture in a continuous flow system, wherein the hydrazine and the oxidant contained in the reaction mixture react to form a diimide and the one or more morphinan alkaloids and the diimide react to form a selectively reduced compound in the continuous flow system, wherein steps are performed in less than about 1 hour, and wherein the reaction step occurs at a temperature greater than about 70° C.

In another embodiment, the present disclosure relates to a process for the selective reduction of one or more olefin compounds, particularly one or more morphinan alkaloids, including the steps of providing a liquid mixture of the one or more olefin compounds, particularly one or more morphinan alkaloids, and hydrazine in a solvent, contacting the liquid mixture with a gaseous oxidant to form a reaction mixture, reacting the hydrazine and the oxidant contained in the reaction mixture to form a diimide in a continuous flow reactor, reacting the one or more olefin compounds, particularly one or more morphinan alkaloids, and the diimide in the reaction mixture to form a selectively reduced compound in the continuous flow system, wherein the all of the steps are performed in less than about 1 hour, and wherein the reaction steps occur at a temperature greater than about 70° C. The selectively reduced compound can thereafter be isolated.

In another embodiment, the process can further include the steps of providing one or more additional liquid mixtures containing additional amounts of hydrazine in solvent, after the initial reaction or subsequent reactions but before isolating the selectively reduced compound, contacting the one or more additional liquid mixtures with the reaction mixture, reacting the additional amounts of hydrazine and oxidant contained in the reaction mixture to form additional amounts of diimide in the continuous flow reactor, and reacting the one or more olefin compounds, particularly one or more morphinan alkaloids, and the additional amounts of diimide in the reaction mixture to form additional amounts of the selectively reduced compound in the continuous flow reactor.

In another embodiment, the process further includes the steps of providing a second liquid mixture containing a second amount of hydrazine in a second solvent, and contacting the second liquid mixture with the reaction mixture, wherein the second amount of hydrazine and oxidant contained in the reaction mixture react to form a second amount of diimide and the one or more olefin compounds, particularly one or more morphinan alkaloids, and the second amount of diimide react to form a second amount of the selectively reduced compound in the continuous flow system.

In another example, the process can further include the steps of providing a second liquid mixture containing a second amount of hydrazine in a second solvent, after the initial reaction but before isolating the selectively reduced compound, contacting the second liquid mixture with the reaction mixture, reacting the second amount of hydrazine and oxidant contained in the reaction mixture to form a second amount of diimide in the continuous flow reactor, and reacting the one or more olefin compounds, particularly one or more morphinan alkaloids, and the second amount of diimide in the reaction mixture to form a second amount of the selectively reduced compound in the continuous flow reactor. In some embodiments, multiple additions of hydrazine and oxidant are added in multiple steps to drive the reaction to at least an acceptable level of conversion (e.g., greater than about 75%, 80%, 85%,90%, 95%, 98% 99%, approaching 100% conversion).

In another embodiment, the present disclosure relates to a process for the selective reduction of one or more olefin compounds, particularly one or more morphinan alkaloids, including the step of providing a liquid mixture of the one or more olefin compounds, particularly one or more morphinan alkaloids, base, and one or more hydrazine-containing compounds in a solvent in a continuous flow reactor, wherein the one or more hydrazine-containing compounds and base contained in the reaction mixture react to form a diimide and the one or more olefin compounds, particularly preferably one or more morphinan alkaloids, and the diimide react to form a selectively reduced compound in the continuous flow system, wherein the process is performed in less than about 1 hour, and wherein continuous flow reactor is at a temperature greater than about 120° C.

In another embodiment, the present disclosure relates to a process for the selective reduction of one or more olefin compounds, particularly one or more morphinan alkaloids, including the steps of providing a liquid mixture of the one or more olefin compounds, particularly one or more morphinan alkaloids, base, and a hydrazine-containing compound, or one or more hydrazine-containing compounds, in a solvent, reacting the hydrazine-containing compound and base contained in the reaction mixture to form a diimide in a continuous flow reactor, reacting the one or more olefin compounds, particularly one or more morphinan alkaloids, and the diimide in the reaction mixture to form a selectively reduced compound in the continuous flow reactor, wherein all of the steps are performed in less than about 1 hour, and wherein the reacting steps occur at a temperature greater than about 120° C. The selectively reduced compound can thereafter be isolated.

In another embodiment, the process can further include the steps of providing one or more additional liquid mixtures containing additional amounts of hydrazine-containing compound in solvent, after the initial reaction or subsequent reactions but before isolating the selectively reduced compound, contacting the one or more additional liquid mixtures with the reaction mixture, reacting the additional amounts of hydrazine-containing compounds and base contained in the reaction mixture to form additional amounts of a diimide in the continuous flow reactor, and reacting the one or more olefin compounds, particularly one or more morphinan alkaloids, and the additional amounts of diimide in the reaction mixture to form additional amounts of the selectively reduced compound in the continuous flow reactor.

In another example, the process can further include the steps of providing a second liquid mixture containing a second amount of hydrazine-containing compound in a second solvent, after the initial reaction but before isolating the selectively reduced compound, contacting the second liquid mixture with the reaction mixture, reacting the second amount of hydrazine-containing compound and base contained in the reaction mixture to form a second amount of diimide in the continuous flow reactor, and reacting the one or more olefin compounds, particularly one or more morphinan alkaloids, and the second amount of diimide in the reaction mixture to form a second amount of the selectively reduced compound in the continuous flow reactor.

The embodiments of the present disclosure address the disadvantages of the prior art, i.e., expensive, uneconomical and unsafe. For example, the use of a continuous flow system reduces or eliminates the safety risks present in traditional batch synthesis, such as those based on the oxidation of hydrazine, including spontaneous ignition resulting in explosions. The small volumes, channel dimensions and/or reduced head space of the continuous flow system can reduce explosion risks and allow a safe process for selective olefin reduction. The methodology of the present disclosure can also be performed without the use of catalysts. In certain embodiments, the continuous flow system using hydrazine and oxygen to generate diimide also produces less problematic by-products. The by-products are predominantly nitrogen, water and, in some cases, dimethylsufoxide produced by the reaction of dimethylsulfide with oxidizing by-products including thebaine-N-oxide and hydrogen peroxide.

BRIEF DESCRIPTION OF THE DRAWINGS

The foregoing and other advantages provided by the present disclosure will be more fully understood from the following description of exemplary embodiments when read together with the accompanying drawings, in which:

FIG. 4 shows the impact of temperature, time and coil material on the reduction of thebaine using a continuous flow system as described in the present disclosure and in Example 1.

FIG. 9 shows the impact of multiple injections on the reduction of thebaine using a continuous flow system as described in the present disclosure and in Example 4.

DETAILED DESCRIPTION

Figure 1:
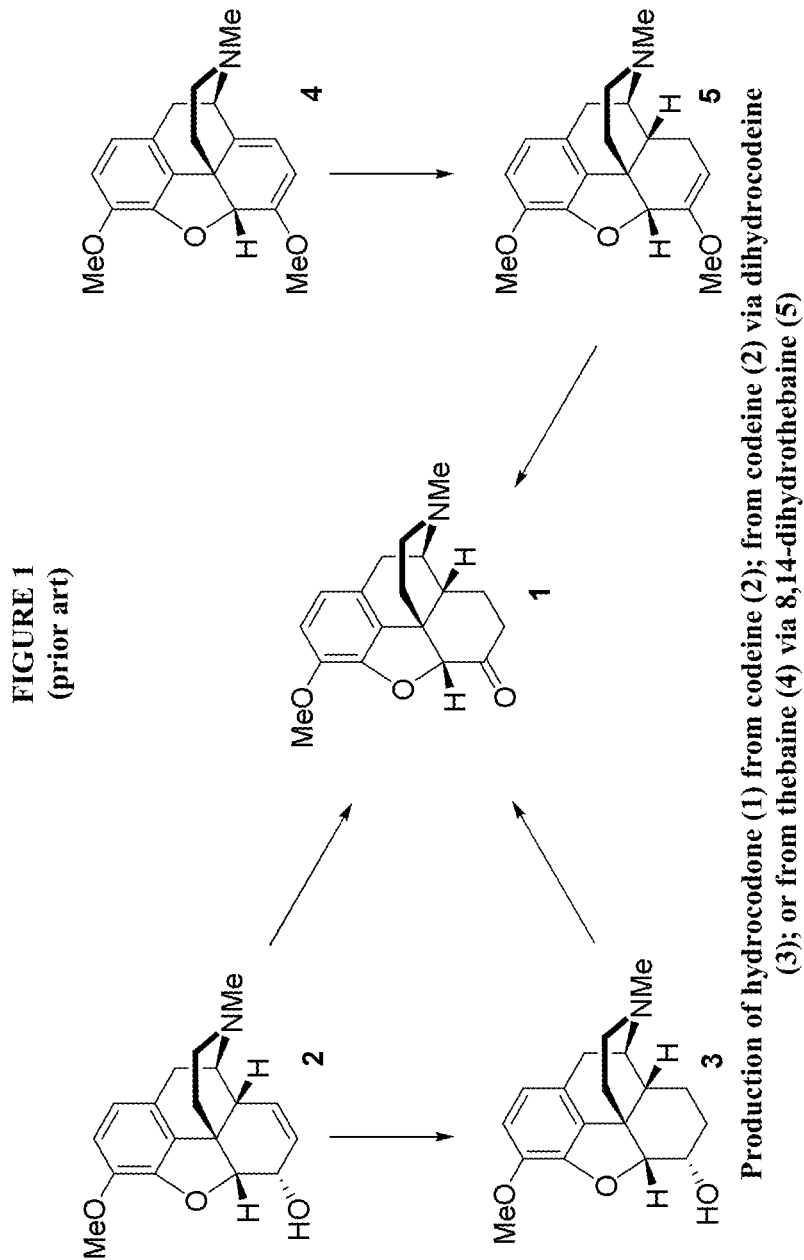
FIG. 1 shows exemplary synthesis routes for the production of hydrocodone (1) from codeine (2); from codeine (2) via dihydrocodeine (3); and from thebaine (4) via 8,14-dihydrothebaine (5).
Figure 2:
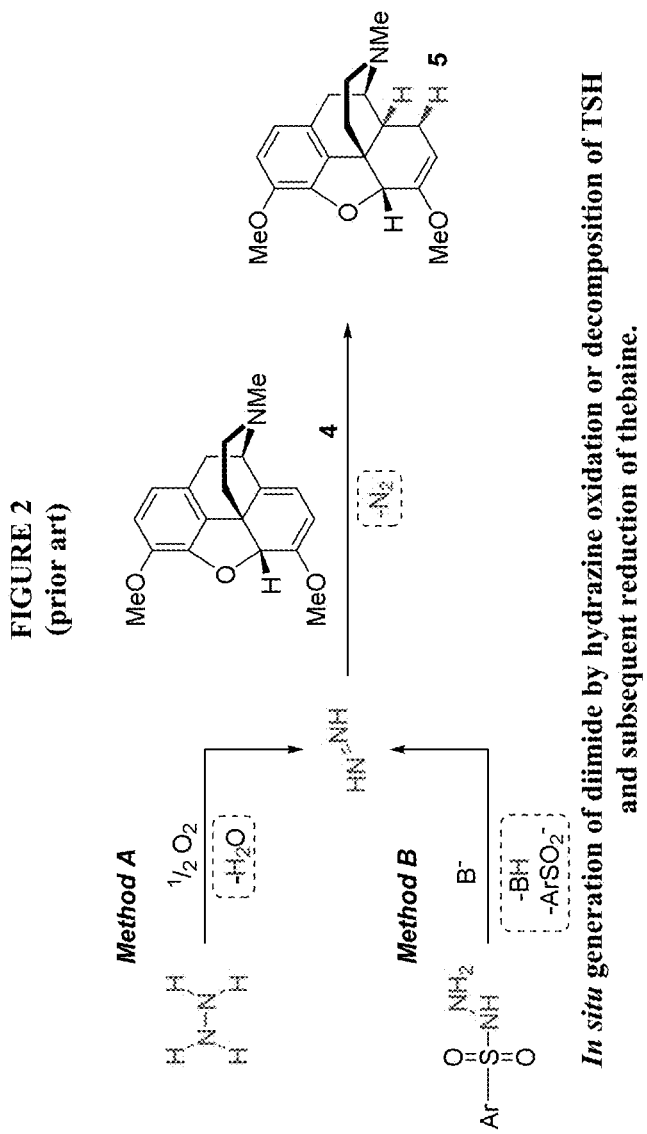
FIG. 2 shows exemplary synthesis routes for the production of 8,14-dihydrothebaine according to the present disclosure. Method A shows the in situ generation of diimide by hydrazine oxidation. Method B shows the in situ generation of diimide by the decomposition of p-toluenesulfonyl hydrazide.

The present disclosure relates to selective reduction of morphinan alkaloids in a continuous flow system. In particular, the present disclosure relates to selective reduction of thebaine using hydrazine or a hydrazine-containing compound in a continuous flow system under elevated temperature and pressure conditions.

As described herein the term "olefin" refers to any compound that includes one or more conjugated or unconjugated double bonds, such as an olefin in an opioid-like structure, particularly a morphinan alkaloid, for example thebaine As described herein the term "morphinan alkaloid" refers to any compound containing the base chemical structure below, also known as the morphinan ring structure.

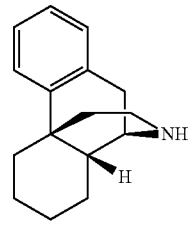 [SMILES: c1ccc2c(c1)C[C@H]1NCC[C@@]23CCCC[C@@H]13]

Suitable examples of a morphinan alkaloid include any one or mixture of one or more of thebaine, codeine, oripavine and morphine. One skilled in the art will recognize that morphinan alkaloids are polar compounds which are high molecular weight (e.g., molecular weight greater than about 250 g/mol).

In one embodiment, the present disclosure relates to a process for the selective reduction of one or more olefin compounds, particularly one or more morphinan alkaloids, including the steps of providing a liquid mixture of the one or more olefin compounds, particularly one or more morphinan alkaloids, and hydrazine in a solvent, and contacting the liquid mixture with a gaseous oxidant to form a reaction mixture in a continuous flow system, wherein the hydrazine and oxidant contained in the reaction mixture react to form diimide and the one or more olefin compounds, particularly one or more morphinan alkaloids, and the diimide react to form a selectively reduced compound in the continuous flow system. In some embodiments, the steps can be performed in less than about 6, 5, 4, 3, 2, or about 1 hour. In some embodiments, the reactions occur at a temperature greater than about 70° C., 80° C., 90° C., 100° C., 110° C., 120° C. or about 130° C., particularly at a temperature in the range of about 110° C. to about 130° C.

In another embodiment, the present disclosure relates to a process for the selective reduction of one or more olefin compounds, particularly one or more morphinan alkaloids, including the steps of providing a liquid mixture of the one or more olefin compounds, particularly one or more morphinan alkaloids, and hydrazine in a solvent, contacting the liquid mixture with a gaseous oxidant to form a reaction mixture, reacting the hydrazine and oxidant contained in the reaction mixture to form a diimide in a continuous flow system, reacting the one or more olefin compounds, particularly one or more morphinan alkaloids, and the diimide in the reaction mixture to form a selectively reduced compound in the continuous flow system. The selectively reduced compound can thereafter be hydrolyzed or isolated for later hydrolysis.

The olefin compound can be any olefin, particularly any morphinan alkaloid, such as thebaine, that is capable of being selectively reduced by a strong reducing agent, such as diimide, in a continuous flow reactor system. The olefin can be a morphinan alkaloid having an unsaturated ring. For example, the olefin can be a compound of the formula (I)

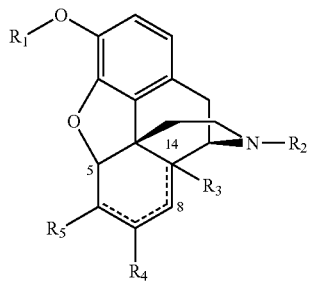

(I)

wherein

R$_1$ is selected from the group consisting of H and C$_{1-10}$alkyl;

R$_2$ is selected from the group consisting of H, C$_{1-10}$alkyl, C$_{2-10}$alkenyl, C$_{1-10}$alkyl-R$_6$ and C$_{2-10}$alkenyl-R$_6$;

R$_3$ is selected from H, OH and C$_{1-10}$alkyl;

R$_4$ and R$_5$ are each independently selected from the group consisting of H, OH, C$_{1-10}$alkyl, C$_{2-10}$alkenyl, C$_{1-10}$alkyl-R$_6$ and C$_{2-10}$alkenyl-R$_6$, O, and O—C$_{1-10}$alkyl, each group being unsubstituted or substituted with one or more substitutes independently selected from O and OH;

any two of R$_3$, R$_4$, and R$_5$ can combine to form an additional ring structure selected from the group consisting of C$_{3-10}$cycloalkyl, C$_{3-10}$heterocycloalkyl, C$_{6-10}$aryl, and C$_{6-10}$heteroaryl;

R$_6$ is selected from the group consisting of C$_{3-10}$cycloalkyl, C$_{3-10}$heterocycloalkyl, C$_{6-10}$aryl, and C$_{6-10}$heteroaryl; and ⁓⁓⁓ represents a single or double bond, provided that at least one double bond is present in either the 7,8 position or the 8,14 position.

In one embodiment, R$_5$ can be selected from the group consisting of OH or O.

In one embodiment, the olefin is an morphinan alkaloid selected from the group consisting of thebaine, oripavine, 14-hydroxycodeinone, 14-hydroxymorphinone, 14-hydroxy-nor-codeinone, 14-hydroxy-nor-morphinone, 7,8-dehydronaltrexone and 7,8-dehydronaloxone. For example, the processes of the present disclosure can be used to reduce oripavine to dihydrooripavine, which can thereafter be hydrolysed to hydromorphone.

The hydrazine can be hydrazine hydrate (e.g., monohydrate), hydrazine anhydrous or different concentrations of hydrazine in water or aqueous based solutions. The one or more olefin compounds, particularly one or more morphinan alkaloids, and hydrazine can be present in a liquid mixture with a solvent. The solvent can be any solvent capable of creating a liquid mixture with the one or more olefin compounds, particularly one or more morphinan alkaloids, and hydrazine and that allows for the generation of diimide upon the combination of the liquid mixture with a gaseous oxidant. The solvent can include C$_1$-C$_5$ alcohols, alkoxy and organic solvents, including alkoxy alkanols and alkoxy alkandiols, such as ethanol, toluene, 2-methoxy-ethanol, ethanol amine, 2-ethoxy-ethanol, isopropanol, 2-propoxy-ethanol, 1-methoxy-2-propanol, 1-methoxy-2-butanol, 3-methoxy-1-butanol, 3-methoxy-3-methyl-1-butanol, 3-methoxy-1,2-propandiol, 1-butanol, 2-butanol, dimethylene glycol dimethyl ether, dietheylene glycol dimethyl ether, water, dimethyl sulfoxide, N,N-dimethyl formamide, dioxane, morpholine, diethyl carbonate, methyl oxitol, diglyme and methyl t-butyl ether, as well as combinations thereof. The solvent can contain a combination of two or more solvents and can be combined in any ratio. For example, a two solvent system can contain 9:1-1:9 v/v of two solvents, hi one embodiment, the solvent comprises toluene and ethanol (e.g., 1:1 or 2:1).

The liquid mixture can contain variable amounts of olefin, particularly a morphinan alkaloid, and hydrazine. The amount of the one or more olefin compounds, particularly one or more morphinan alkaloids, in the liquid mixture can be about 0.05, 0.1, 0.15, 0.2, 0.25, 0.3, 0.35, 0.4, 0.45, 0.5, 0.6, 0.7, 0.8, 0.9 or about 1 M. These values can be used to define a range, such as about 0.25 to about 0.4 M. The amount of hydrazine in the liquid mixture can be about 0.2, 0.3, 0.4, 0.5, 0.6, 0.7, 0.8, 0.9, 1, 1.5, 2, 2.5, 3, 3.5 or about 4 M, These values can be used to define a range, such as about 1 to about 2 M.

The hydrazine or hydrazine-containing compound can be present in the liquid mixture in excess of the one or more olefin compounds (either the actual olefin content or the starting olefin content). The liquid mixture can contain about 1, 1.5, 2, 2.5, 3, 3.5, 4, 4.5, 5, 5.5, 6, 6.5, 7, 7.5, 8, 8.5, 9, 9.5 or 10 equivalents of hydrazine or hydrazine-containing compound to olefin. These values can also be used to define a range, such as about 1.5 to about 3, or about 3 to about 4 equivalents of hydrazine or hydrazine-containing compound to olefin. As used herein, unless otherwise noted, the term 'equivalents of olefin' shall mean molar equivalents of olefin compound.

The liquid mixture can be contacted with a gaseous oxidant to form a reaction mixture using a continuous flow reactor system. The flow rate of the liquid mixture can vary depending on the dimensions of the continuous flow reactor system and to maintain efficient conversion and formation of the selectively reduced compound. The liquid mixture flow rate can be about 1, 5, 10, 50, 100, 200, 300, 400, 500, 600, 700, 800, 900 or about 1,000 μL/min. These values can also be used to define a range, such as about 300 to about 500 μL/min.

The size and material of the tubing containing the liquid mixture and/or throughout the continuous flow reactor system can also vary depending on the type of reagents used, products produced and to maintain efficient conversion and formation of the selectively reduced compound. The size of the tubing can be about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90 or about 100 mm internal diameter (i.d.). These values can also be used to define a range, such as about 0.5 to about 1 mm i.d. The material of the tubing can be an inert plastic, such as perfluoroalkoxy, a composite material, a metal, such as stainless steel, or combinations thereof.

The gaseous oxidant can be any gaseous oxidant capable of reacting with hydrazine to produce diimide. In one embodiment, the gaseous oxidant is oxygen gas. The flow rate of the gaseous oxidant can vary depending on the dimensions of the continuous flow reactor system and to maintain efficient conversion and formation of the selectively reduced compound. The oxygen stream flow rate can be about 1, 5, 10, 20, 30, 40, 50, 60, 70, 80, 90 or about 100 mL/min. These values can also be used to define a range, such as about 30 to about 50 mL/min. The amount of gaseous oxidant present in the reaction mixture can be 1, 2, 3, 4, 5, 6, 7, 8, 9, 10, 11, 1.2, 13, 14, 15, 16, 17, 18, 19, 20, 21, 22, 23, 24 or about 25 equivalents of the olefin. These values can also be used to define a range, such as about 8 to about 15 equivalents.

The hydrazine and the oxidant can be reacted in a continuous flow reactor system to form diimide. The reaction can occur in one or more residence time units (RTU) each independently having a length of tubing or coil and heated to an elevated temperature. The length of tubing or coil can be characterized by volume. The length of tubing or coil can contain a volume of about 1 mL, 2, 3, 4, 5, 6, 7, 8, 9, 10, 15, 20, 25, 30, 35, 40, 45 or about 50 mL. These values can also be used to define a range, such as about 5 to about 50 mL. The temperature of each RTU unit, or the continuous flow reactor system, can be about, or greater than about 30, 40, 50, 60, 70, 80, 90, 100, 110, 120, 130, 140, 150, 160, 170, 180, 190 or about 200° C. These values can also be used to define a range, such as about 80° C. to about 140° C. The temperature can also be a few degrees (e.g., 1-10 degrees) below the degradation temperature of the reagents or desired products. In one embodiment, the continuous flow system contains three RTUs. The first and second RTU can have a 10 mL length of tubing and be held at 100° C. The third RTU can have a 20 mL length of tubing and be held at 120° C.

Once diimide is formed in the reaction mixture, it can react with the one or more olefin compounds, particularly one or more morphinan alkaloids, in the reaction mixture to form a selectively reduced compound. The amount of selectively reduced compound can be increased by adding additional amounts of hydrazine to the reaction mixture after the initial reaction with diimide has occurred. The additional amounts of hydrazine can react with the oxidant to form additional diimide, which can subsequently react to form additional amounts of the selectively reduced compound. In one embodiment, the process of the present disclosure can further include providing a second liquid mixture containing a second amount of hydrazine in a second solvent after the initial reaction, contacting the second liquid mixture with the reaction mixture, resulting in the reaction of the second amount of hydrazine and oxidant contained in the reaction mixture to form a second amount of diimide in the continuous flow system, and the reaction of the one or more olefin compounds, particularly one or more morphinan alkaloids, and the second amount of diimide in the reaction mixture to form a second amount of the selectively reduced compound in the continuous flow system. The additional hydrazine introduced can have a similar or different flow rate, relative concentration, solvent or combinations thereof, as described for the initial conditions.

In another embodiment, the process of the present disclosure can further include providing one or more additional liquid mixtures containing additional amounts of hydrazine in solvent after the initial or subsequent reaction(s), contacting the one or more additional liquid mixtures with the reaction mixture, resulting in the reaction of the additional amounts of hydrazine and oxidant contained in the reaction mixture to form additional amounts of diimide in the continuous flow system, and reaction of the one or more olefin compounds, particularly one or more morphinan alkaloids, and the additional amounts of diimide in the reaction mixture to form additional amounts of the selectively reduced compound in the continuous flow system. The additional hydrazine amounts introduced can each have a similar or different flow rate, relative concentration, solvent or combinations thereof, as described for the initial conditions. In one embodiment, the steps of the present disclosure are performed in a continuous manner, In some embodiments, the hydrazine or hydrazine-containing compound can be present in one or more feeds in 0.5, 1, 1.5, 2, 2.5, 3, 3.5, 4, 4.5, 5, 6, 7, 8, 9 or about 10 equivalents of the olefin (e.g., thebaine). These values can also be used to define a range, such as about 2 to about 5 equivalents. Similarly, in other embodiments, the oxidant can be present in the reaction mixture can be 1, 2, 3, 4, 5, 6, 7, 8, 9, 10, 11, 12, 13, 14, 15, 16, 17, 18, 19, 20, 21, 22, 23, 24 or about 25 equivalents of the olefin (e.g., thebaine). These values can also be used to define a range, such as about 8 to about 15 equivalents.

During the reduction reactions described in the present disclosure hydrogen peroxide can be generated as a by-product. The hydrogen peroxide can convert the one or more olefin compounds, particularly one or more morphinan alkaloids, to an N-oxide and limit the formation of the selectively reduced compound. In one embodiment, the hydrogen peroxide can convert thebaine to thebaine-N-oxide and reduce the formation of dihydrothebaine. The addition of an oxygen scavenger, such as dimethyl sulfide, can convert the N-oxide compound back to the olefin compound, particularly the morphinan alkaloid, to allow it to be reduced.

In some embodiments, the reaction mixture can include a scavenger or antioxidant additive. The scavenger or antioxidant can be any scavenger or antioxidant that allows for the efficient conversion and formation of the selectively reduced compound and reduces the production of by-products, such as N-oxides. The scavenger or antioxidant can be dimethyl sulfide or triethylamine. The scavenger or antioxidant additive can be present in the reaction mixture in 1, 2, 3, 4, 5, 6, 7, 8, 9, 10, 11, 12, 13, 14, 15, 16, 17, 18, 19, 20, 21, 22, 23, 24 or about 25 equivalents of the olefin. These values can also be used to define a range, such as about 5 to about 15 equivalents. In other embodiments, multiple additions of hydrazine, oxygen and dimethylsulfide can be used, in part, to introduce additional amounts of an oxygen scavenger into the system.

The percent conversion of the one or more olefin compounds, particularly one or more morphinan alkaloids, to the selectively reduced compound, after one or more additions of hydrazine, can be greater than about 50%, 55%, 60%, 65%, 70%, 75%, 80%, 85%, 90%, 91%, 92%, 93%, 94%, 95%, 96%, 97%, 98% or about 99%. These values can also define a range, such as about 92% to about 98%.

The selective reduction of the one or more olefin compounds, particularly one or more morphinan alkaloids, can include the reduction of an unsaturated bond in a ring structure. In one embodiment, the selectively reduced compound is 8,14-dihydrothebaine, 8,14-dihydrooripavine, 14-hydroxycodeineone, 14-hydroxymorphinone, codeine or morphine.

After the reaction, the selectively reduced compound can be isolated according to known methods, for example by purification, separation or isolation methodology, including chromatography, crystallization, extraction, precipitation, filtration, or combinations thereof. The selectively reduced compound in the reaction mixture or after isolation can be further reacted to form additional compounds. In one embodiment, the process of the present disclosure relates to the formation of hydrocodone by hydrolyzing the selectively reduced compound 8,14-dihydrothebaine, in an acid aqueous solution, in the reaction mixture or after being isolated from the crude reaction mixture. The process of the present disclosure can further include adding or introducing an acid aqueous solution to the reaction mixture in the continuous flow system to allow for the hydrolysis of the selectively reduced compound to an active pharmaceutical ingredient, such as hydrocodone or hydromorphone.

The process of the present disclosure can efficiently form the selectively reduced compound (e.g., 8,14-dihydrothebaine) or a further reacted compound (e.g., hydrocodone) in a high yield per the starting material. Similarly, the process of the present disclosure can efficiently form the selectively reduced compound (e.g., 8,14-dihydro-oripavine from oripavine) or a further reacted compound (e.g., hydromorphone) in a high yield per the starting material. The yield of the selectively reduced compound or the further reacted compound is greater than about 70%, 71%, 72%, 73%, 74%, 75%, 76%, 77%, 78%, 79%, 80%, 80%, 81%, 82%, 83%, 84%, 85%, 86%, 87%, 88%, 89%, 90%, 91%, 92%, 93%, 94%, 95%, 96%, 97%, 98% or about 99%. These values can define a range, such as about 90% to about 99%. These conversion and yields can be obtained in a relatively short time. The selectively reduced compound or the further reacted compound, at a high conversion or yield, can be achieved in less than about 6 hours, 4, 3, 2, 1, 0.9, 0.8, 0.7, 0.6, 0.5, 0.4, 0.3, 0.2 or about 0.1 hours. These values can also be used to define a range, such as about 0.3 to about 1 hour. These values can also be used to describe the residence time of the components within the continuous flow system and/or the contacting time between the liquid mixture and the gaseous oxidant. In one embodiment, the continuous flow system includes multiple (e.g., 4) consecutive liquid feeds of hydrazine or hydrazine containing compound (e.g., hydrazine hydrate) and residence time units resulting in a highly selective reduction within less than one hour.

The continuous flow system, one or more of the reactions in the continuous flow system, or combinations thereof can be carried out under elevated pressure. The system pressure can be maintained by one or more pumps and back pressure regulators contained in the system. The system pressure can be about 2, 3, 4, 5, 6, 7, 8, 9, 10, 15, 20, 25, 30, 35, 40, 45, 50, 60, 70, 80, 90 or about 100 bar. These values can also be used to define a range, such as about 2 to about 20 bar, or about 15 to about 40 bar.

One advantage of using hydrazine hydrate and an oxidant to generate the diimide is the reduction of chemical waste, thereby making the process sustainable for large scale/commercial manufacture. The methodology of the present disclosure can also be applied to the use of a hydrazine-containing compound, such as p-toluenesulfonyl hydrazide, as the diimide precursor to generate the diimide. One advantage of this methodology is the elimination of a gaseous reagent.

In one embodiment, the present disclosure relates to a process for the selective reduction of one or more olefin compounds, particularly one or more morphinan alkaloids, including the steps of providing a liquid mixture of the one or more olefin compounds, particularly one or more morphinan alkaloids, base, and one or more hydrazine-containing compounds, in a solvent, wherein the hydrazine-containing compound and base contained in the reaction mixture react to form diimide in a continuous flow system, and the one or more olefin compounds, particularly one or more morphinan alkaloids, and the diimide in the reaction mixture react to form a selectively reduced compound in the continuous flow system. The selectively reduced compound can thereafter be isolated and/or hydrolyzed in the continuous flow system, as provided above. The process conditions, reagents, products, etc. can be similar to the conditions, reagents, products, etc. as described for the process using hydrazine and a gaseous oxidant. In another embodiment, the step of providing a liquid mixture of the one or more olefin compounds, particularly one or more morphinan alkaloids, base, and one or more hydrazine-containing compounds in a solvent in a continuous flow system results in the reaction of the one or more hydrazine-containing compounds and base contained in the reaction mixture to form diimide, which diimide thereafter reacts with the one or more olefin compounds, particularly one or more morphinan alkaloids, in the reaction mixture to form a selectively reduced compound in the continuous flow system.

The hydrazine-containing compound can be any organic hydrazine that can be reacted or decomposed in the continuous flow reactor system to generate diimide. The hydrazine-containing compound can be a sulfonyl hydrazide, a aryl sulfonic acid hydrazide in which the aryl group is a benzene or naphthalene that can be mono or poly alkyl substituted, or an alkyl sulfonic acid hydrazide such as methane sulfonic hydrazide or others with branched or unbranched alkyl groups (see, e.g., U.S. Pat. Nos. 3,182,132; 8,399,671; U.S. Patent Application No. 20060009479 and U.S. Patent Application No. 20150252052, the disclosures of each incorporated herein in their entirety). In some embodiments, the hydrazine-containing compound is p-toluenesulfonyl hydrazide or 2,4,6-triisopropylbenzene sulfonyl hydrazide.

One of the advantages of generating diimide in situ using a hydrazine-containing compounds, such as p-toluenesulfonyl hydrazide, without the addition of an oxidant is the prevention of N-oxide formation.

The hydrazine-containing compound can be reacted or decomposed with a base. The base can be any base that can react or decompose the hydrazine-containing compound in the continuous flow reactor system to generate diimide. The base can be an alkali metal hydroxide or an organic base such as ethanolamine, morpholine, ethylenediamine, or 1,3-propanediamine.

In particular embodiments, the present disclosure describes a scalable methodology for the reduction of thebaine by in situ generating diimide from either hydrazine or from p-toluenesulfonyl hydrazide (as the diimide precursor) and oxygen. The hydrazine/oxygen route to form diimide is disfavored on an industrial scale due to safety concerns in batch mode. The continuous flow reactor system and method of the present disclosure allow for the safe reduction of thebaine by in situ generating diimide from hydrazine and oxygen. The addition of an antioxidant, such as dimethyl sulfide, further reduces the formation of undesired N-oxides. The present disclosure also improves the reduction procedure using p-toluenesulfonyl hydrazide the diimide precursor by utilizing a continuous flow reactor system. Both methodologies of the present disclosure allow for a highly selective reduction of the desired or targeted double bond, for example in less than about 6, 4, 2 or about 1 hour. The resulting selectively reduced compound, e.g., 8,14-dihydrothebaine, can be further processed or converted, e.g., converted into hydrocodone by subsequent hydrolysis.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

Thebaine Reduction Using Hydrazine Hydrate

Figure 3:
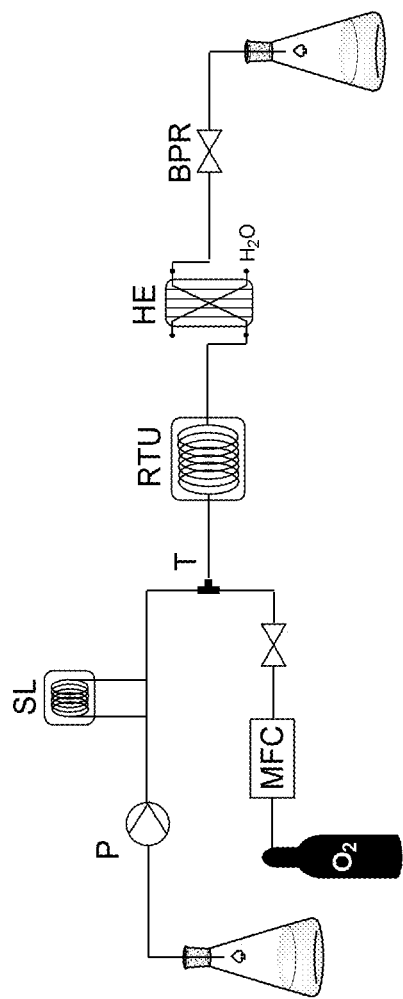
FIG. 3 shows an exemplary continuous flow system for the in situ generation of diimide and subsequent reduction as described in the present disclosure and in Example 1.

The reduction of thebaine was carried out using a gas/liquid continuous flow reactor FIG. 3 shows an exemplary gas/liquid continuous flow reactor system. A commercially available reactor system (FlowSyn, Uniqsis Ltd) and additional syringe pumps (Asia pumping module, Syrris) were used and modified. A liquid stream was pumped using a HPLC pump (P) and mixed with oxygen gas in a T-piece (T) mixer. The oxygen gas (e.g, gaseous oxidant) was delivered by a standard compressed gas cylinder and the flow was controlled by a mass flow controller (MFC). A sample loop (SL) was connected to the liquid stream via a 6-way-valve and used to introduce the thebaine/hydrazine solution to the liquid stream. The liquid stream and oxygen gas were mixed to form a gas/liquid reaction mixture. The reaction mixture was passed through a heated residence time unit (RTU). The reaction mixture was then cooled to room temperature in a heat exchanger (HE) and depressurized by passing through a backpressure regulating unit (BPR). The back pressure was controlled using either static or adjustable regulation units.

Flow experiments were carried out using a liquid stream flow rate of 400 μL/min and an oxygen gas flow rate of 40 ml/min. These flows resulted in a stable segmented flow pattern at a system pressure of about 25 bar. Thebaine has a low solubility in most organic solvents, including alcohols can be used for in olefin reduction reactions. Therefore, the solvent comprised toluene and ethanol. A mixture of toluene/ethanol (2:1) was used. The sample loop was preheated to about 70° C. to ensure a homogenous solution of thebaine and hydrazine hydrate was introduced to the liquid stream. At room temperature, the thebaine and hydrazine hydrate solution became slowly biphasic after the addition of hydrazine hydrate.

A series of experiments were performed varying the reaction temperature in the RTU and the RTU coil material. The temperature was varied from 50° C. to 140° C. (e.g., near the degradation temperature of thebaine). A 10 mL perfluoroalkoxy coil (PFA, 0.8 mm i.d.; 1.6 mm o.d.) or a 20 mL stainless steel coil was used in the residence time unit. The concentration of thebaine in the liquid mixture was about 0.5 mmol. The concentration of hydrazine hydrate (i.e., $N_2H_4.H_2O$) in the liquid mixture was about 2 mmol (or about 4 equivalents of hydrazine hydrate to thebaine). The oxygen gas was present in excess of both thebaine and hydrazine (e.g., about 12 equivalents of thebaine), The reaction products were collected, tested and quantified by HPLC-UV (215 nm) by peak area percent. Analytical HPLC analysis was carried out on a C-18 reversed-phase (RP) analytical column (150×4.6 mm, particle size 5 μm) at 37° C. using a mobile phase A (water/acetonitrile 90:10 (v/v)+0.1% TFA) and B (MeCN+0.1% TPA) at a flow rate of 1.0 mL/min at an isocratic flow using 5% solvent B for 21 min. Afterwards the amount of solvent B was increased to 100% within 1 min and kept at this ratio for 4 min. Column chromatography was carried out using an automated flash chromatography system (Isolera, Biotage) using dichloromethane/methanol mixtures as eluent.

FIG. 4 shows the reaction of thebaine (4) to form the desired 8,14-dihydrothebaine (5) as well as N-oxide by-products of thebaine (6) and (7). Compound (7) is the hydrogenated analog of (6). As shown in FIG. 4, a reaction temperature of 50° C. using PFA tubing resulted in a 10 minute residence time in the MIT and a selective reaction (FIG. 4, Entry-1) as only 8,14-dihydrothebaine (5) was formed. The conversion, however, was low as only 9% of 8,14-dihydrotbebaine (5) was formed. When the temperature was increased to 100° C. the residence time increased to 12 minutes (FIG. 4, Entry 2) and N-oxides were formed, it is believed the residence time got longer at the elevated temperature due to the increased gas permeability of PFA. The identification of the by-products was determined by LC-MS. It is believed that N-oxides were formed by the generation of peroxide in the system in an unidentified side-reaction.

Since N-oxides can easily be reduced to amines by standard reagents (e.g., $NaBH_4$, $LiAlH_4$) additional heat was added to investigate increasing the conversion of thebaine (4) to the hydrogenated N-oxide analog (7). At temperatures above 120° C. the reaction mixture almost exclusively contained the oxidized by-products (6) and (7). The overall amount of double bond reduction and formation of the hydrogenated analog (7) did not increase significantly (FIG. 4, Entries 3 and 4). At the upper temperature limit of 140° C. using PEA tubing the reaction did not result in a selective reduction having a high conversion rate (FIG. 4, Entry 4). The 10 mL PFA tubing was replaced with 20 mL stainless steel tubing in the residence time unit. It was believed that the combination of higher temperatures and higher pressures can be achieved using a stainless steel tubing. It was also believed that the residence time would not vary since gas permeability through the PFA tubing was eliminated.

Two additional experiments were performed using the stainless steel tubing at 120° C. and at 140° C. At 120° C., a highly selective reduction occurred without the formation of detectable amounts of the respective N-oxide by-products (FIG. 4, Entry 5). By increasing the temperature to 140° C. slightly higher conversions were obtained while maintaining the high selectivity (FIG. 4, Entry 6). Both experiments (FIG. 4, Entries 5 and 6) had a residence time of about 10 min which is significantly shorter than experiments using the PFA tubing with a smaller volume under otherwise identical conditions. It is believed that the selectivity may be caused by small amounts of $Fe^{2+}$ being formed on the coil surface which readily decomposes any generated peroxide in the system circumventing selectivity issues. Unfortunately, the use of stainless steel tubing was also less reproducible over time than PFA tubing, A steel passivation procedure using $HNO_3$ (20% v/v) was required with the stainless steel tubing to generate reproducible results.

Example 2

Thebaine Reduction Using Hydrazine Hydrate and an Additive

Figure 5:
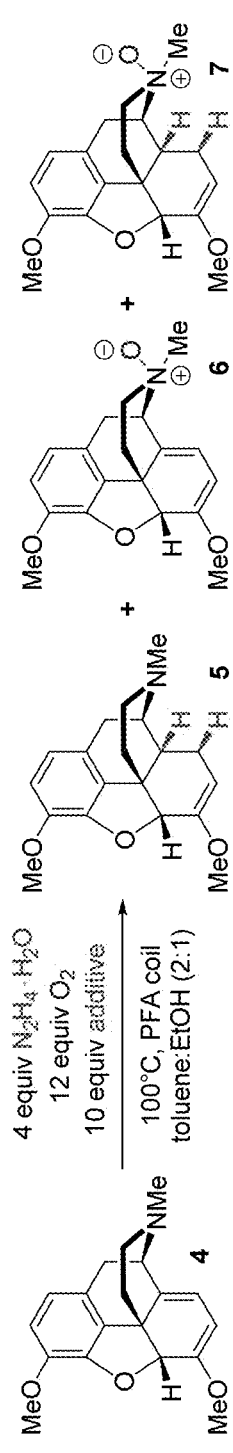
FIG. 5 shows the impact of additives, pressure and oxygen gas flow on the reduction of thebaine using a continuous flow system as described in the present disclosure and in Example 2.

A set of experiments using PFA tubing (10 and 13 mL) was performed using the gas/liquid continuous flow reactor system as described in Example 1. The system pressure, the oxygen gas stoichiometry and use of an antioxidant additive were tested. The temperature for each of these experiments was 140° C., just under the decomposition temperature of thebaine. In some embodiments, the temperature was 100° C. The additive was included in the liquid mixture to capture the formed hydrogen peroxide in a simultaneous oxidation. A simple amine (i.e., $Et_3N$) and a sulfide (i.e., $Me_2S$) were each tested as the additive. Each are known to be oxidized by hydrazine hydrate/oxygen combinations. FIG. 5 shows the impact of additives, pressure and oxygen gas flow on the reduction of thebaine in the continuous flow system. When triethylamine was used in excess (about 10 equiv) very low quantities of the oxidized side products were observed (FIG. 5, Entry 2). The double bond reduction, however, was less efficient than without an additive (FIG. 5, Entries 1 2). When dimethyl sulfide was used in excess (about 10 equiv), a comparable amount of olefin reduction occurred simultaneously improving the selectivity (FIG. 5, Entry 3).

Additional experiments were performed varying the amount of applied back pressure and oxygen gas stoichiometry to reduce the amount of N-oxide by-product formation. The back pressure was reduced from 25 bar to 17 bar while simultaneously changing the tubing length from 13 mL to 10 mL to obtain a comparable residence time (FIG. 5, Entry 4). The double bond reduction was not significantly affected but the formation of N-oxide by-products was reduced indicating a pressure dependency. Lowering the oxygen flow to 20 mL/min (corresponding to about 6 equiv) resulted in a slightly higher conversion but also a comparably longer residence time (FIG. 5, Entry 5), namely 25 minutes versus 12 minutes. Next, both the oxygen gas flow (10 mL/min, 3 equiv) and the back pressure were decreased thereby reducing the amount of amine oxidation within a reasonable reaction time (FIG. 5, Entry 6). A reduced amount of N-oxide byproducts were formed and a higher degree of olefin reduction was achieved. Further lowering of the oxygen flow (5 mL/min, 1.5 equivalents) increased the residence time significantly but had a negligible effect on conversion and selectivity (FIG. 5, Entry 7).

Example 3

Thebaine Reduction Using Hydrazine Hydrate, Reduced Pressure and an Additive

Figure 6:
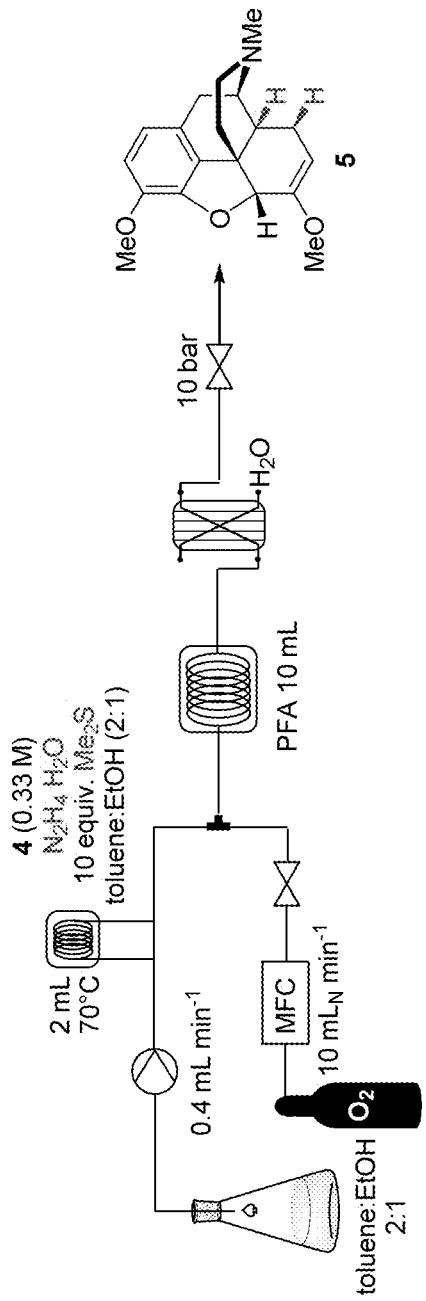
FIG. 6 shows the impact of temperature and hydrazine stoichiometry on the reduction of thebaine using a continuous flow system as described in the present disclosure and in Example 3.

A set of experiments using PFA tubing (10 a reduced pressure profile and the additive was performed using the gas/liquid continuous flow reactor system as described in Example 1. FIG. 6 shows the impact of temperature and hydrazine stoichiometry on the reduction of thebaine in the continuous flow system. The combination of the PFA tubing, the lowered oxygen flow of 10 mL/min (3 equiv), the lowered back pressure of 10 bar and the addition of dimethyl sulfide (10 equiv) provided a reduction of thebaine with moderate conversion and practically no by-product formation (FIG. 6, Entry 1). The double bond reduction was subsequently improved by increasing the temperature from 100° C. to 120° C. resulting in about 70% conversion while maintaining the high selectivity (FIG. 6, Entry 2). The effect of reducing the amount of hydrazine hydrate was tested by reducing to 3 equivalents without any influence on the reaction rate (FIG. 6, Entry 3). Yet, further reductions showed a reduction in conversion as it is believed that lower amounts of the diimide precursor was present (FIG. 6, Entry 4). An increase to the maximum possible temperature for thebaine (e.g., 140° C.) gave similar results as experiments at 120° C. (FIG. 6, Entries 5, 6 and 7).

Figure 7:
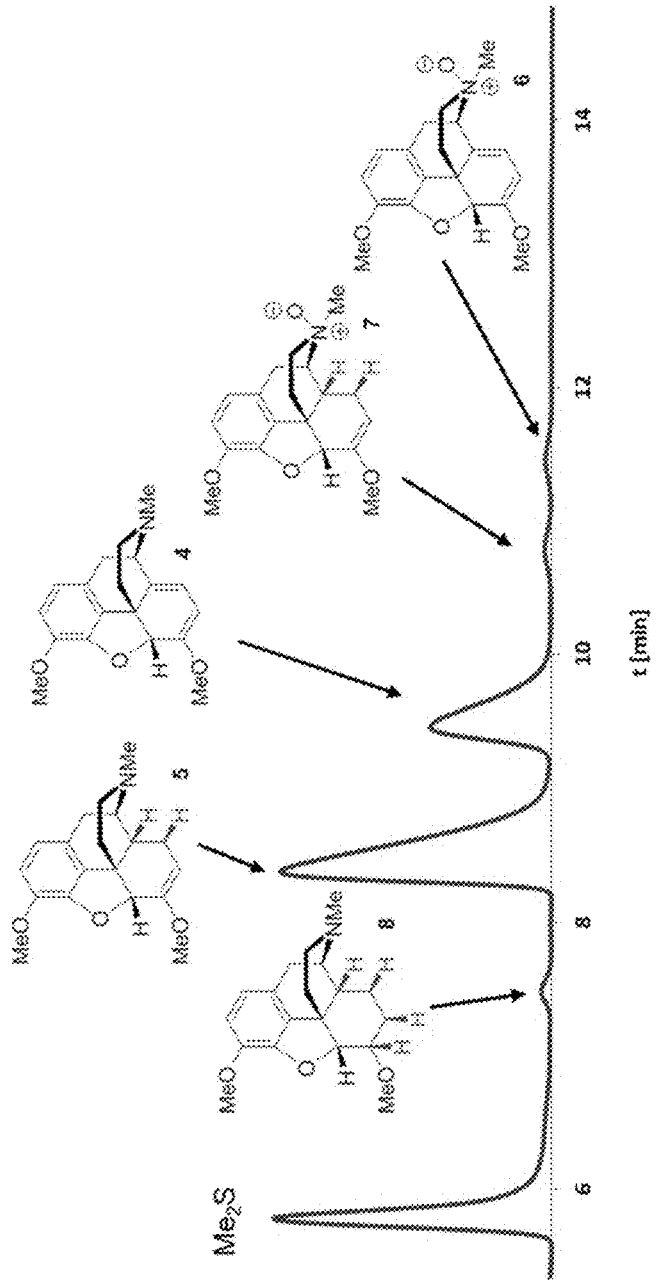
FIG. 7 shows an exemplary HPLC-UV chromatogram (215 nm) of the thebaine reduction products using a continuous flow system as described in the present disclosure and in Example 3.

For each of the reactions in Example 3 and FIG. 6, the amount of undesired N-oxides was either below 1% or not detectable. The only other by-product observed (present up to about 1%) appeared to be the over-reduced tetrahydrothebaine (8). FIG. 7 shows the HPLC-UV chromatogram (215 nm) of the thebaine reduction with diimide at 10 bar and 120° C. in the presence of dimethyl sulfide. The structures of the reagent, product and by-products are shown, including thebaine (4), 8,14-dihydrothebaine (5), N-oxides of thebaine (6) and (7), and tetrahydrothebaine (8).

Example 4

Thebaine Reduction Using Hydrazine Hydrate, an Additive and Multiple Injections

Figure 8:
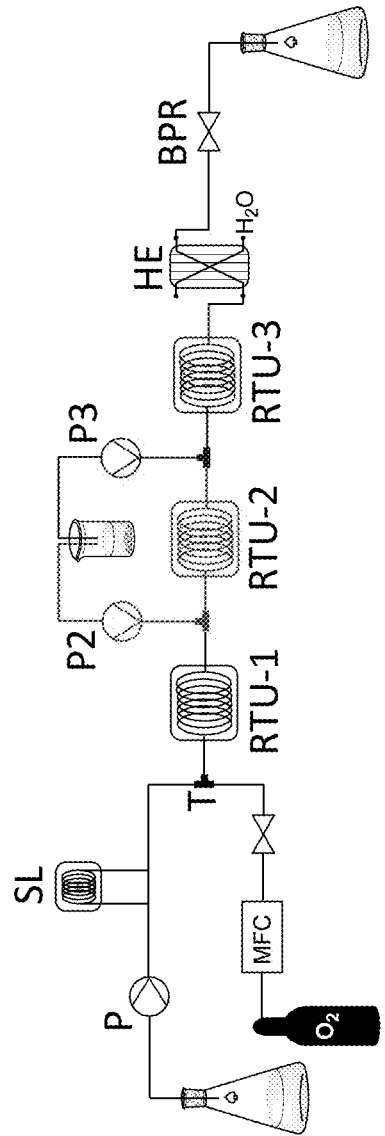
FIG. 8 shows an exemplary multi-injection continuous flow system for the in situ generation of diimide having two additional feeds (i.e., P2 and P3) with the respective residence time units (i.e., RTU-2 and RTU-3).

A set of experiments was performed using the gas/liquid continuous flow reactor system as described in Example 1 and having additional pumps and heated residence time units as shown in FIG. 8. FIG. 8 shows an exemplary multi-injection continuous flow system for the in situ generation of diimide. The multi-injection continuous flow system is extended by additional feeds or pumps (P2 and P3) and respective residence time units (RTU-2 and RTU-3). The objective of reducing thebaine using the multi-injection continuous flow system is to drive the reaction to completion and achieve quantitative reduction is a multi-injection approach. The multiple injection reduces the amount of diimide disproportionation due to a reduced hydrazine/diimide concentration along the reactor and enables an increased reaction time since under the continuous high-temperature/high-pressure conditions most of the hydrazine hydrate is consumed within less than about 10 min.

The experiments varied the number of additional injections and amount of hydrazine hydrate. The experiments were carried out using a liquid mixture having a flow rate of 400 μL/min and containing 0.5 mmol thebaine, hydrazine hydrate (3 equiv), dimethyl sulfide (10 equiv) in toluene:EtOH (2:1). The liquid mixture was combined with oxygen gas having a flow rate of 10 mL/min to form a reaction mixture. The reaction mixture was reacted in a first heated residence time unit (RTU-1) at 120° C. The system pressure was held at 10 bar. For each additional injection or feed of hydrazine, a 3.2M hydrazine hydrate solution (3 equiv) in EtOH was pumped at a flow rate of 0.1 mL/min. FIG. 9 shows the impact of multiple injections on the reduction of thebaine on the continuous flow system. In FIG. 9, Entry 6, a 1M hydrazine hydrate solution (1 equiv) in EtOH was pumped at a flow rate of 0.1 mL/min.

The first multi-injection experiment (FIG. 9, Entry 1) used the temperature and pressure settings as described in Example 3 (e.g., FIG. 6, Entry 3) and was carried out by installing one supplementary hydrazine hydrate feed delivering an additional 3 equivalents of the diimide precursor before passing through a second 10 mL residence time unit (e.g., P2 and RTU-2 only). The conversion was increased from about 70% to over 80% indicating that the multi-injection strategy was successful. The experiment was repeated adding pure EtOH instead of a hydrazine hydrate solution (FIG. 9, Entry 2) to test if the longer residence time was a factor. As expected, the prolonged reaction time alone does not increase the conversion. A lower oxygen flow of 5 mL/min (1.5 equiv) was also tested. The lower oxygen flow produced less olefin reduction and a longer reaction time (FIG. 9, Entry 3). The multi-injections were stepwise expanded in the continuous flow multi-addition reactor resulting in about 94% conversion using four (4) liquid feeds, four (4) residence time units and 12 equivalents of the diimide precursor in total (FIG. 9, Entry 5). The conversion rate was tested using a reduced amount of hydrazine hydrate (e.g., three additional feeds of 1 equiv rather than 3 equiv). The reduced hydrazine hydrate feeds resulted in a conversion drop below 90% (FIG. 9, Entry 6). A fifth liquid feed was also tested. The additional liquid feed did not further improve the continuous reaction. (FIG. 9, Entry 7).

For the multi-injection experiment using four liquid feeds, four residence time units and 12 equivalents of the diimide precursor, such as in (FIG. 9, Entry 5), the increasing overall reactor volume had a non-linear effect on residence time. The amount of gas decreases constantly along the reactor coil and the segmented pattern disappeared completely at a certain point. In the case of experiment (FIG. 9, Entry 5) the reaction mixture passed the first coil within about 6 minutes, the second after about 8 minutes, the third after about 10 minutes and the last coil after about 13 min. It is believed that the gas-permeability of the PFA tubing and the additional solvent from the additional feeds affect the non-linear residence time. The additional amount of solvent within the system can dissolve more gas and affect the influence of the gas on the overall flow rate.

After achieving a 90%+ conversion, the reaction mixture containing 8,14-dihydrothebaine was directly hydrolyzed in 6N Ha at room temperature. The 8,14-dihydrothebaine was converted to hydrocodone. Analysis by HPLC-UV indicated that 8,14-(dihydrothebaine was quantitatively hydrolyzed within 30-60 minutes whereas thebaine and the over-reduced side product tetrahydrothebaine were not affected.

Example 5

Figure 10:
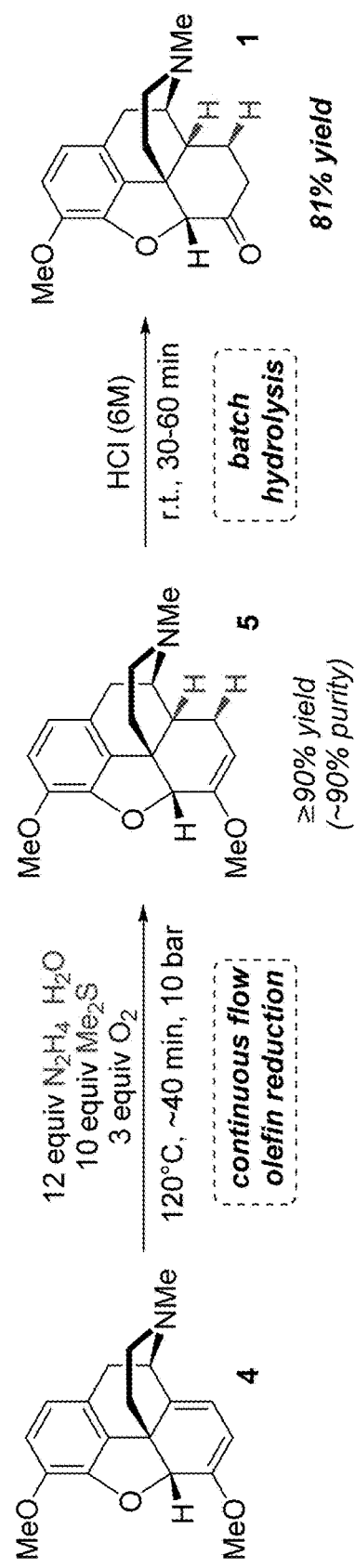
FIG. 10 shows an exemplary continuous transfer hydrogenation and batch hydrolysis for the synthesis of hydrocodone from thebaine as described in the present disclosure and in Example 5.
Figure 11:
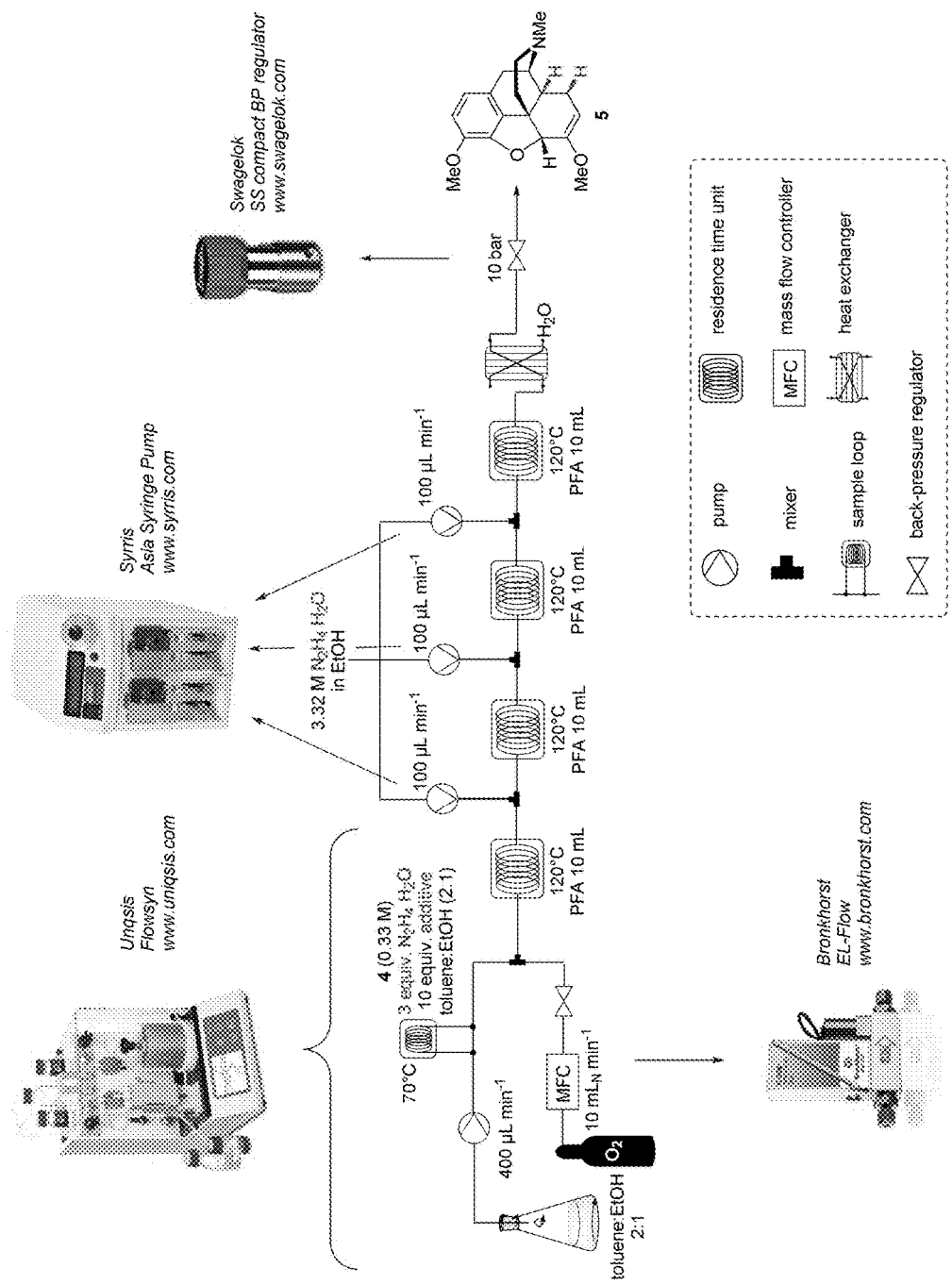
FIG. 11 shows an exemplary continuous flow reactor system having additional pumps and heated residence time units as described in the present disclosure and in Example 5.

Synthesis of Hydrocodone From Thebaine and Hydrazine Hydrate in a Multi-Injection Continuous Flow System The synthesis of hydrocodone from thebaine and hydrazine hydrate in a multi-injection continuous flow system was performed. FIG. 10 shows an overall reaction summary. FIG. 11 shows an exemplary gas/liquid continuous flow reactor system having additional pumps and heated residence time units.

Continuous Reduction: A continuous flow process was utilized having a liquid feed (toluene/ethanol (2:1)) and a gaseous feed (oxygen gas, purity 5.0). Thebaine (2.00 mmol, 622.9 mg), dimethyl sulfide (10.0 mmol, 738.2 μL) and hydrazine hydrate (6.00 mmol 291.7 μL) were dissolved in toluene/ethanol (2:1) to a total volume of 6 mL. The resulting solution was stirred and heated to 70° C. until it became homogeneous. The solution was injected in a preheated sample loop (70° C.) which was connected to the liquid feed via a 6-way valve. The liquid mixture (400 μL/min) and the gaseous feed (10 mL/min) were mixed together in a T-mixer to form a reaction mixture. The resulting segmented reaction mixture was passed through a PFA reactor coil (0.8 mm inner diameter, 10 mL reactor volume) at 120° C. After passing through the coil, a T-mixer connected another feed adding hydrazine hydrate in EtOH (3.2 M) at a flow rate of 100 μL/min to the reaction mixture. The combined stream passed through an additional 10 mL PFA reactor coil at 120° C. Two additional hydrazine hydrate feeds were added to the reaction mixture resulting in a continuous flow reactor system having three additional hydrazine hydrate feeds and an overall reactor volume of 40 mL. After passing through the last PFA reactor coil, the reaction mixture was cooled in a heat exchanger with water as cooling agent. After passing a back pressure regulator holding the system to a pressure of 10 bar, the solution was collected. The reaction mixture was concentrated under reduced pressure resulting in a light brown solid which was dissolved in 20 mL $CHCl_3$. The solution was extracted twice with slightly basic water (2×20 mL; pH=8-9) to remove residual hydrazine hydrate. The unreacted hydrazine was removed to avoid hydrazine reacting with hydrocodone and forming the corresponding hydrazone or azine. The organic phase was dried over $Na_2SO_4$ and the solvent was removed resulting in 609 mg of a brown solid containing >90% 8,14-dihydrothebaine according to $^1$H-NMR Hydrolysis: The crude mixture was dissolved in 6 M HCl (5 mL) and the resulting dark orange solution was stirred until HPLC analysis showed that the 8,14-dihydrothebaine was totally consumed (30-60 min). The acidic solution was diluted with $H_2O$ (10 mL) and extracted with $Et_2O$ (30 mL) to remove organic impurities. Afterwards, 3 M NaOH was added until the pH of the aqueous solution was >10. Extraction with $CHCl_3$ (3×20 mL) resulted in an orange solution. After solvent evaporation a yellowish solid with a HPLC purity of ~93% (1-2% THT or tetrahydrothebaine, 5-6% thebaine) was obtained. Purification by flash column chromatography using a dichloromethane/methanol gradient (containing 1% v/v $Et_3N$) finally resulted in a 81% yield (484.2 mg, 1.62 mmol) of hydrocodone as a pile-yellow solid.

$^1$H-NMR and $^{13}$C spectra were recorded on a 300 MHz instrument using $CDCl_3$ as solvent. Chemical shifts (δ) are expressed in ppm downfield from TMS as internal standard. The letters s, d, t, q, qt and in are used to indicate a singlet, doublet, triplet, quadruplet, quintuplet and multiplet, respectively. $^1$H NMR (300 MHz, $CDCl_3$) δ 6.72 (d, J=8.2 Hz, 1H), 6.65 (d, 8.2 Hz, 1H), 4.68 (s, 1H), 3.92 (s, 3H), 3.20 (m, 1H), 3.04 (d, J=18.5 Hz, 1H), 2,59 (m, 2H), 2.49-2.27 (m, 6H), 2.21 (td, J=11.9, 3.3 Hz, 1H), 2.08 (td, J=12.0, 4.5 Hz, 1H), 1.86-1.79 (m, 2H), 1.35-1.19 (m, 1H). $^{13}$C NMR (75 MHz, $CDCl_3$) δ 207.89, 145.39, 142.82, 127.24, 126.28, 119.76, 114.47, 91.39, 59.19, 56.75, 56.71, 46.89, 46.83, 42,88, 42.70, 40.23, 35,52, 25.57, 19.95.

Example 6

Additional Additives Tested

A set of experiments was performed using the gas/liquid continuous flow reactor system and conditions as described in Examples 1 and 5. A variety of additives were tested including ethanolamine, morpholine, pyridine, DMSO, N,N'-dimethylthiourea or diphenylsulfide. The reaction mixture combined 0.5 mmol thebaine in 1.5 mL toluene:EtOH (2:1) having a 0.4 mL/min flow with an oxygen gas having a 10 mL/min flow. The reaction temperature was 120° C. The three (3) additional hydrazine feeds contained 3.2M hydrazine hydrate in EtOH and were pumped at 0.1 mL/min.

Figure 12:
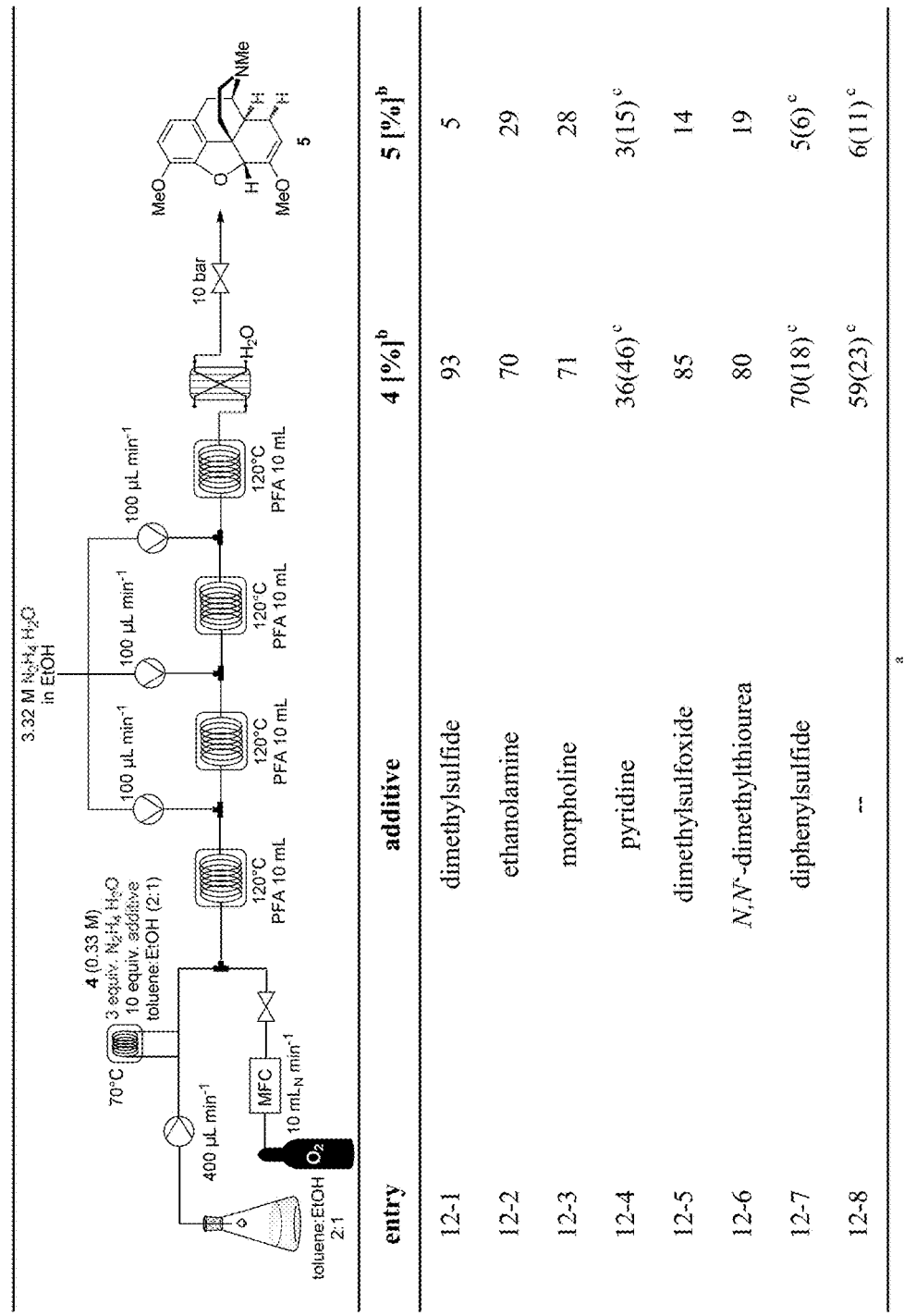
FIG. 12 shows the impact of additional antioxidant additives on the reduction of thebaine using a continuous flow system as described in the present disclosure and in Example 6.

FIG. 12 shows the results of the experiments. All of the tested additive produced lower conversions or unselective reductions. The total amount of N-oxide by-products formed is listed in the parentheses.

Example 7

Thebaine Reduction Using p-Toluenesulfonyl Hydrazine (TSH)

Figure 13:
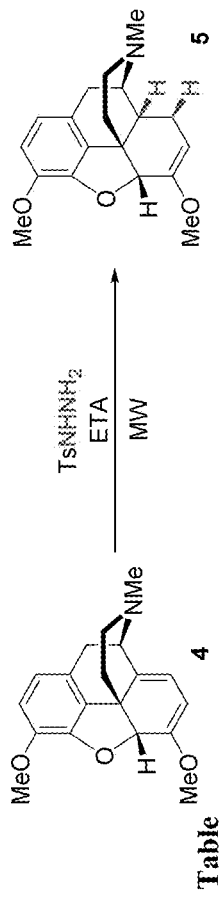
FIG. 13 shows the impact of solvent type and reagent concentrations on batch experiments for the reduction of thebaine using p-toluenesulfonyl hydrazide as described in Example 7.

The reduction of thebaine was investigated using p-toluenesulfonyl hydrazide (TSH) as the diimide precursor using a dedicated microwave reactor (e.g., batch experiments). Microwave-assisted reactions were carried out in a Biotage initiator 2.5 instrument in Pyrex vessels (2-5 mL) controlling the reaction temperature by an external IR sensor. The initial reaction involved combining thebaine (0.2 mmol-0.4 mmol in ethanol) with 2 equivalents of both ethanolamine (ETA) and TSH to form a mixture. The mixture was inhomogeneous. The inhomogeneous mixture was heated for 20 min at 70° C. In some embodiments, the mixture was heated to 100° C. The initial reaction produced a selective hydrogenation at a reasonable conversion (FIG. 13, Entry 1). The reaction and experimental results are shown in FIG. 13.

The temperature of the reaction was increased to 120° C. and again to 130° C. (FIG. 13, Entries 2 and 3). The conversion was greatest, 94%, at a temperature of 120° C. The only detectable by-product was small amounts of tetrahydrothebaine, less than 1%, Additional experiments were performed using toluene/ethanol (1:1) as the solvent and varying the base and TSH amounts, and the reaction time. (FIG. 13, Entries 4 to 10). Only a reduced reaction time of 10 minutes significantly affected the reaction. In general, the reduction proceeds very fast within the first 20 min resulting in 90%+conversion. Longer reaction times did convert the remaining thebaine into 8,14-dihydrothebaine, but at a slower pace (FIG. 13, Entries 6 and 7). Increasing the amount of TSH, the base equivalents, or both compounds simultaneously did not result in a complete reduction of thebaine (FIG. 13, Entries 8, 9 and 10).

Example 8

Thebaine Reduction Using p-Toluenesulfonyl Hydrazine (TSH)

Figure 14:
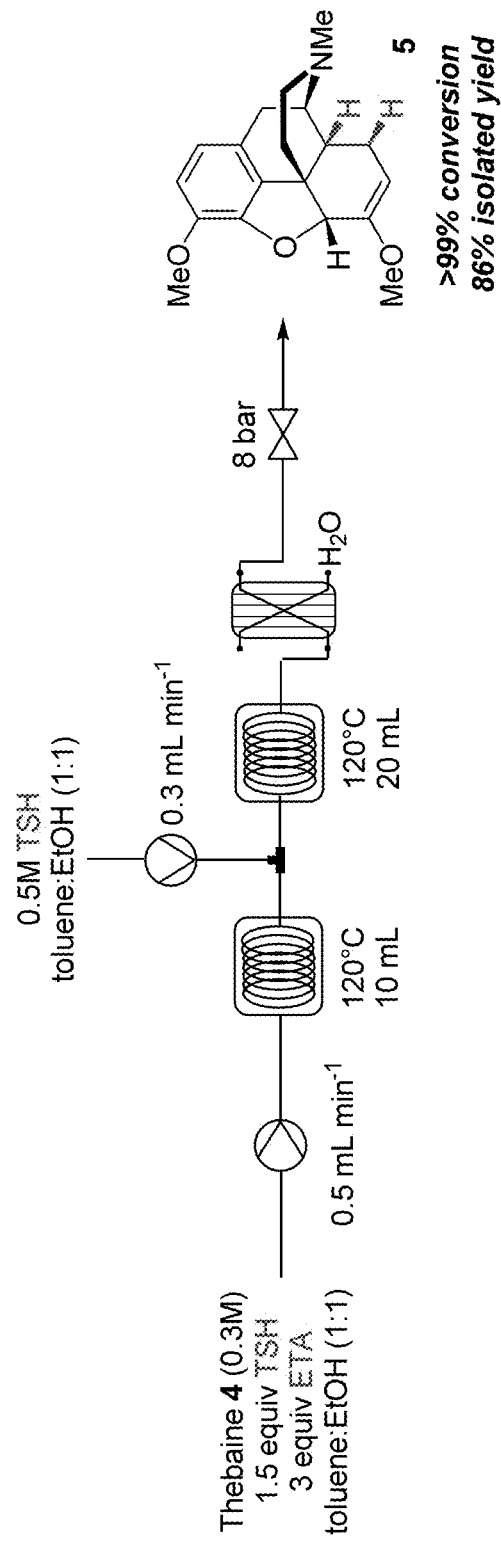
FIG. 14 shows an exemplary continuous flow system for the continuous transfer hydrogenation of thebaine using p-toluenesulfonyl hydrazide as described in the present disclosure and in Example 8.
Figure 15:
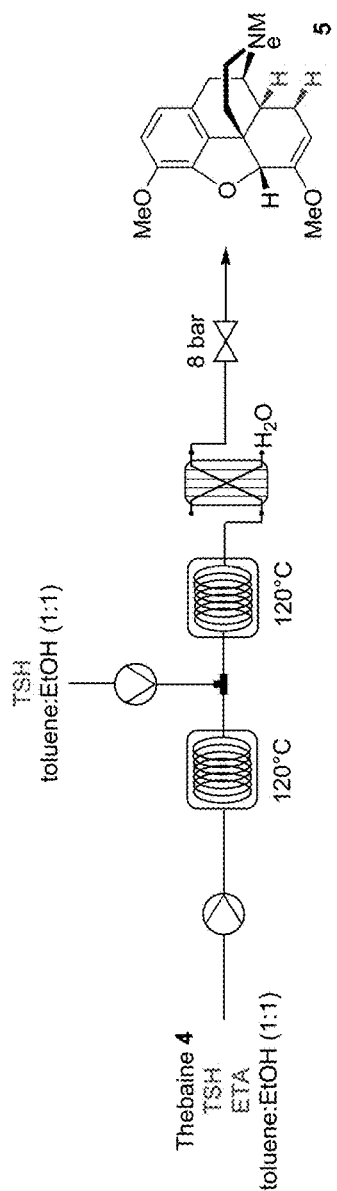
FIG. 15 shows the impact of multiple injections and reagent concentrations on the reduction of thebaine using a continuous flow system as described in the present disclosure and in Example 8.

As set of experiments was performed for the reduction of thebaine using p toluenesulfonyl hydrazide in the gas/liquid continuous flow reactor system described in Example 1, and with the addition of a single additional feed of TSH. FIGS. 14 and 15 shows overviews of the experimental design.

A reaction mixture was formed containing 0.3 M thebaine, ETA (3 equiv) and TSH (1.5 equiv) in toluene:EtOH (1:1) solvent. The reaction mixture flow rate was 0.5 mL/min through the continuous flow reactor system. The reaction mixture was pumped through a first heated residence time unit at 120° C. having a 10 mL PFA tubing. In some experiments, after passing through the residence time unit, a T-mixer connected a feed adding 0.5 M TSH in toluene:EtOH (1:1) at a flow rate of 0.3 mL/min to the reaction mixture. The combined reaction mixture was passed through an a second heated residence time unit 120° C. having a 20 mL PFA tubing. The reaction mixture was subsequently cooled in a heat exchanger and depressurized by passing a backpressure regulating unit. The backpressure regulator held the system pressure at 8 bar.

The results of the experiments are shown in FIG. 15. Without the additional feed, higher amount of base and TSH were needed to achieve high conversions. With the additional feed, lower amount of base and TSH were used to achieve a high conversion in the same amount of time. The use of two amounts of TSH at 1.5 equivalents resulted in a quantitative reaction carried out within 45 min. Subsequent crystallization was used to isolate 8,14-dihydrothebaine in 86% yield as a colorless solid.

The reduction of thebaine using p-toluenesulfonyl hydrazide in the gas/liquid continuous flow reactor system, as described, is a simple experimental design using less pumps and residence time units than the reduction using hydrazine/oxygen gas. Both reductions, however, successfully reduced thebaine. The reduction of thebaine using p-toluenesulfonyl hydrazide in the gas/liquid continuous flow reactor system, as described, also uses lower amounts of diimide precursor to reduce thebaine. Yet, the hydrazine/oxygen gas route generates solely benign chemical byproducts (water and nitrogen gas).

Example 9

Figure 16:
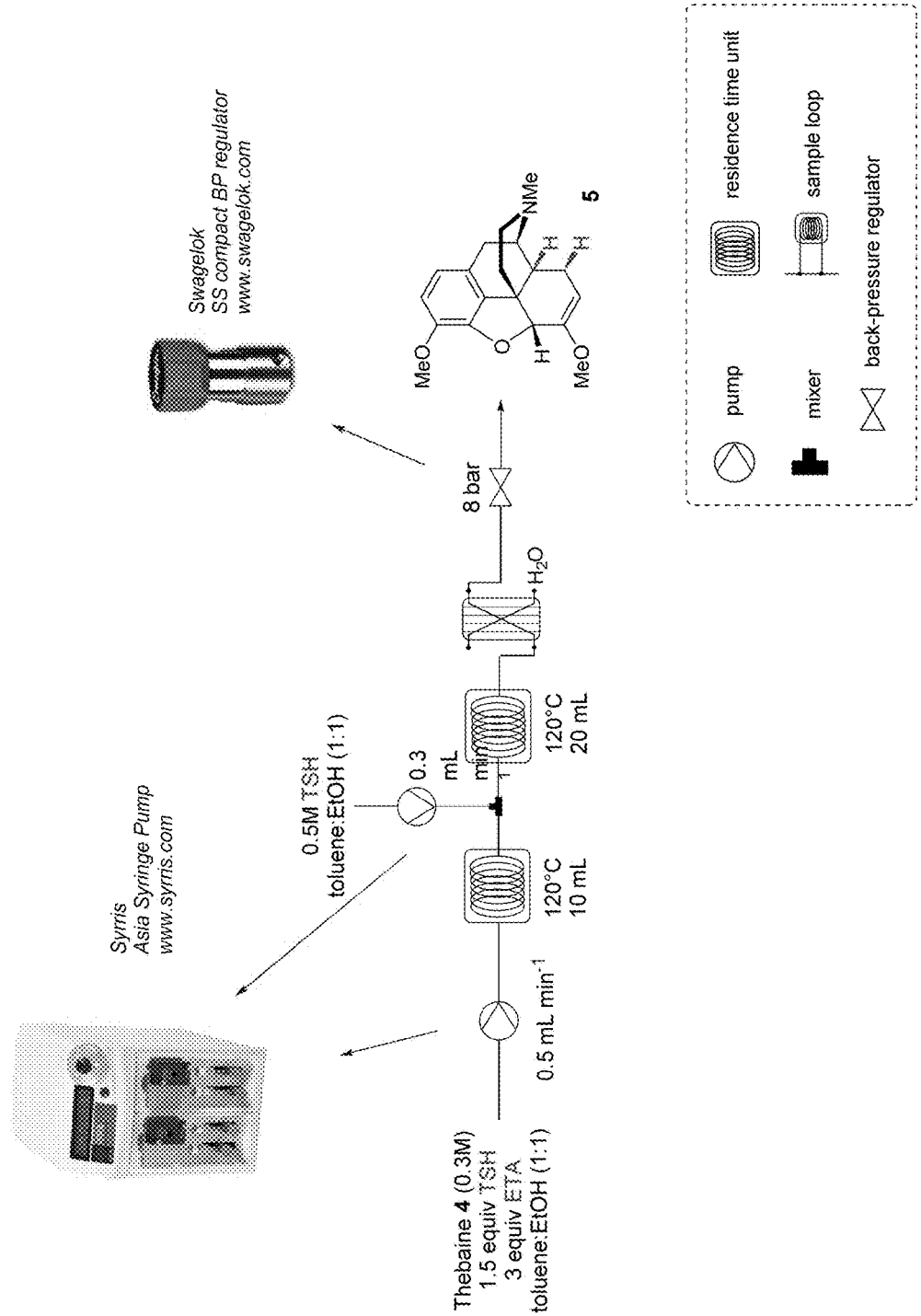
FIG. 16 an exemplary continuous flow reactor system having an additional pump and heated residence time unit as described in the present disclosure and in Example 9.

Reduction of Thebaine With p-Toluenesulfonyl Hydrazide and Ethanolamine in a Multi-Injection Flow System The reduction of thebaine with TSH in a multi-injection continuous flow system was performed. FIG. 16 shows an exemplary gas/liquid continuous flow reactor system having an additional pump and heated residence time unit.

Continuous Reduction: A continuous flow process was utilized by passing a reaction mixture (flow rate 500 µL/min) containing thebaine (623.4 mg, 2.00 mmol), p-toluenesulfonyl hydrazide (559.26 mg, 3.00 mmol) and ethanolamine (363 µL, 6.00 mmol) dissolved in toluene:ethanol (1:1) to give a total volume of 6.6 mL through first residence time unit having PFA tubing (0.8 mm inner diameter, 10 mL reactor volume) at 120° C. After passing through the first residence time unit, a T-mixer connected another feed adding p-toluenesulfonyl hydrazide in toluene:ethanol (1:1, 0.5 M) at a flow rate of 300 µL/min to the reaction mixture. The combined reaction mixture was passed through a second residence time unit having PFA tubing (20 mL) at 120° C. The mixture was then cooled in a heat exchanger with water as cooling agent. After passing a back pressure regulator holding the system pressure at 8-10 bar, the mixture was collected, concentrated under reduced pressure and the residue dissolved in a minimum of EtOH. Deionized water (15 mL) was added and the pH adjusted to >9 with concentrated ammonium hydroxide. The resulting precipitate was isolated by filtration, washed with $H_2O$ and dried in a desiccator resulting in a 86% yield (536.3 mg, 1.71 mmol) of 8,14-dihydrothebaine as a colorless solid. $^1$H NMR (300 MHz, CDCl$_3$) δ 6.72 (d, J=8.2 Hz, 1H), 6.63 (d, J=8.2 Hz, 1H), 4.86 (s, 1H), 4.75 (m, 1H), 3.87 (s, 3H), 3.51 (s, 3H), 3.16 (m 1H), 3.04 (d, J =18.6 Hz, 1H), 2.56 (m, 1H), 2.48-2.23 (m, 6H), 2.06-1.90 (m, 2H), 1.84 (m, 1H), 1.59 (m, 1H), $^{13}$C NMR (75 MHz, CDCl$_3$) δ 152.27, 145.17, 143.09, 129.27, 126.92, 118.54, 113.56, 98.04, 88.56, 59.04, 56.49, 54.35, 46.51, 43.07, 42.48, 39.78, 35.72, 23.61, 20.24.

While this disclosure has been particularly shown and described with reference to example embodiments thereof, it will be understood by those skilled in the art that various changes in form and details may be made therein without departing from the scope of the invention encompassed by the appended claims.

We claim:

1. A process for the selective reduction of one or more morphinan alkaloids comprising the steps of:
   (i) providing a liquid mixture of the one or more morphinan alkaloids, hydrazine and a scavenger in a solvent; and
   (ii) contacting the liquid mixture with a gaseous oxidant to form a reaction mixture in a continuous flow system, wherein the hydrazine and oxidant contained in the reaction mixture react to form diimide and the one or more morphinan alkaloids and the diimide react to form a selectively reduced compound, wherein the contacting time between the liquid mixture and the oxidant is less than about 1 hour, and wherein step (ii) occurs at a temperature greater than about 70° C.;
   wherein said one or more morphinan alkaloids are a compound of formula (I)

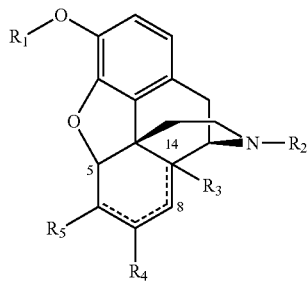

wherein:
R₁ is selected from the group consisting of H and $C_{1-10}$ alkyl;
R₂ is selected from the group consisting of H, $C_{1-10}$ alkyl, $C_{2-10}$ alkenyl, $C_{1-10}$ alkyl-R₆ and $C_{2-10}$ alkenyl-R₆;
R₃ is selected from H, OH and $C_{1-10}$ alkyl;
R₄ and R₅ are each independently selected from the group consisting of H, OH, $C_{1-10}$ alkyl, $C_{2-10}$ alkenyl, $C_{1-10}$ alkyl-R₆ and $C_{2-10}$ alkenyl-R₆, O, and O—$C_{1-10}$ alkyl, each group being unsubstituted or substituted with one or more substitutes independently selected from O and OH;
any two of R₃, and R₅ can combine to form an additional ring structure selected from the group consisting of $C_{3-10}$ cycloalkyl, $C_{3-10}$ heterocycloalkyl, $C_{6-10}$ aryl, and $C_{6-10}$ heteroaryl; and
R₆ is selected from the group consisting of $C_{3-10}$ cycloalkyl, $C_{3-10}$ heterocycloalkyl, $C_{6-10}$ aryl, and $C_{6-10}$ heteroaryl; and ----- represents a single or double bond, provided that at least one double bond is present in either the 7,8 position or the 8,14 position.

2. The process of claim 1, wherein the contacting time between the liquid mixture and the oxidant is less than about 20 minutes.

3. The process of claim 1, wherein step (ii) occurs at a temperature greater than about 120° C.

4. The process of claim 1, further comprising isolating the selectively reduced compound.

5. The process of claim 1, further comprising the steps of:
(iii) providing a second liquid mixture containing a second amount of hydrazine in a second solvent; and
(iv) contacting the second liquid mixture with the reaction mixture, wherein the second amount of hydrazine and oxidant contained in the reaction mixture react to form a second amount of diimide and the one or more morphinan alkaloids and the second amount of diimide react to form a second amount of the selectively reduced compound.

6. The process of claim 5, further comprising the steps of:
(v) providing one or more additional liquid mixtures containing additional amounts of hydrazine in solvent;
(vi) after step (iv), contacting the one or more additional liquid mixtures with the reaction mixture, wherein the additional amounts of hydrazine and oxidant contained in the reaction mixture react to form additional amounts of diimide and the one or more morphinan alkaloids and the additional amounts of diimide react to form additional amounts of the selectively reduced compound.

7. The process of claim 1, wherein the scavenger is dimethyl sulfide.

8. The process of claim 1, wherein the one or more morphinan alkaloids is thebaine, and the selectively reduced compound is 8,14-dihydrothebaine.

9. The process of claim 1, wherein the one or more morphinan alkaloids is oripavine, and the selectively reduced compound is 8,14-dihydrooripavine.

10. The process of claim 1, wherein the oxidant is oxygen gas.

11. The process of claim 8, further comprising the step of hydrolyzing the 8,14-dihydrothebaine to form hydrocodone.

12. The process of claim 9, further comprising the step of hydrolyzing the 8,14-dihydrooripavine to form hydromorphone.

13. The process of claim 4, wherein the yield of the selectively reduced compound is greater than 80%.

14. The process of claim 1, wherein the steps in the continuous flow system are carried out under elevated pressure.

15. The process of claim 1, wherein the solvent comprises toluene and ethanol.

16. The process of claim 1, wherein the steps are performed in a continuous manner.

17. The process of claim 1, wherein the continuous flow system comprises a section of tubing made from a fluorinated or perfluorinated alkylene polymer.

18. A process for the selective reduction of one or more morphinan alkaloids comprising the step of:
providing a liquid mixture of the one or more morphinan alkaloids, base, and one or more hydrazine-containing compounds in a solvent in a continuous flow reactor, wherein the one or more hydrazine-containing compounds and base contained in the liquid mixture react to form diimide and the one or more morphinan alkaloids and the diimide react to form a selectively reduced compound, wherein the process is performed in less than about 1 hour, and wherein the continuous flow reactor is at a temperature greater than about 120° C.,
wherein said one or more morphinan alkaloids are a compound of formula (I)

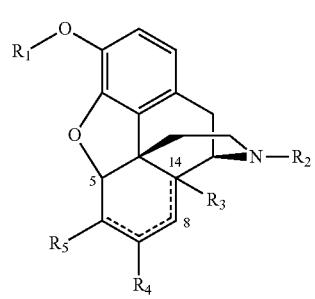

wherein:
R₁ is selected from the group consisting of H and $C_{1-10}$ alkyl;
R₂ is selected from the group consisting of H, $C_{1-10}$ alkyl, $C_{2-10}$ alkenyl, $C_{1-10}$ alkyl-R₆ and $C_{2-10}$ alkenyl-R₆;
R₃ is selected from H, OH and $C_{1-10}$ alkyl;
R₄ and R₅ are each independently selected from the group consisting of H, OH, $C_{1-10}$ alkyl, $C_{2-10}$ alkenyl, $C_{1-10}$ alkyl-R₆ and $C_{2-10}$ alkenyl-R₆, O, and O—$C_{1-10}$ alkyl, each group being unsubstituted or substituted with one or more substitutes independently selected from O and OH;

any two of $R_3$, and $R_5$ can combine to form an additional ring structure selected from the group consisting of $C_{3-10}$ cycloalkyl, $C_{3-10}$ heterocycloalkyl, $C_{6-10}$ aryl, and $C_{6-10}$ heteroaryl; and $R_6$ is selected from the group consisting of $C_{3-10}$ cycloalkyl, $C_{3-10}$ heterocycloalkyl, $C_{6-10}$ aryl, and $C_{6-10}$ heteroaryl; and ----- represents a single or double bond, provided that at least one double bond is present in either the 7,8 position or the 8,14 position.

19. The process of claim 18, wherein the process is performed in less than about 20 minutes.

20. The process of claim 18, further comprising isolating the selectively reduced compound.

21. The process of claim 18, wherein the one or more morphinan alkaloids is thebaine, and the selectively reduced compound is 8,14-dihydrothebaine.

22. The process of claim 18, wherein the one or more morphinan alkaloids is oripavine, and the selectively reduced compound is 8,14-dihydrooripavine.

23. The process of claim 18, wherein the one or more hydrazine-containing compounds comprise p-toluenesulfonyl hydrazide.

24. The process of claim 18, wherein the base is ethanolamine.

25. The process of claim 21, further comprising the step of hydrolyzing the 8,14-dihydrothebaine to form hydrocodone.

26. The process of claim 22, further comprising the step of hydrolyzing the 8,14-dihydrooripavine to form hydromorphone.

27. The process of claim 19, wherein the yield of the selectively reduced compound is greater than 80%.

* * * * *